United States Patent [19]

Rokach et al.

[11] 4,263,207

[45] Apr. 21, 1981

[54] 10,11-DIHYDRODIBENZO[b,f][1,4]THIAZEPINE CARBOXYLIC ACIDS ESTERS AND AMIDES THEREOF

[75] Inventors: Joshua Rokach, Chomedey-Laval, Canada; Edward J. Cragoe, Jr., Lansdale; Clarence S. Rooney, Worcester, both of Pa.

[73] Assignee: Merck & Co., Inc., Rahway, N.J.

[21] Appl. No.: 930,107

[22] Filed: Aug. 1, 1978

[51] Int. Cl.$^3$ .................. C07D 00/00; C07D 281/04; C07D 265/30

[52] U.S. Cl. ............................ 260/239.3 T; 260/330; 260/243.3

[58] Field of Search ............. 260/327 B, 330, 239.3 T, 260/243.3; 544/111

[56] References Cited

PUBLICATIONS

Kawashima et al., C. A. 79, 137209a (1973) Abst. of Japanese Pat. Kokci, 73 52,786, 7-1973.

Primary Examiner—Donald G. Daus
Assistant Examiner—D. B. Springer
Attorney, Agent, or Firm—Thomas E. Arther; Frank M. Mahon; Julian S. Levitt

[57] ABSTRACT

Novel dibenzo[b,f][1,4]thiazepine derivatives are employed in the treatment and control of allergic conditions such as allergic asthma.

21 Claims, No Drawings

10,11-DIHYDRODIBENZO[b,f][1,4]THIAZEPINE CARBOXYLIC ACIDS ESTERS AND AMIDES THEREOF

This invention relates to new and useful compositions of matter classifiable in the field of organic chemistry as dibenzothiazepines. More particularly, the instant invention relates to a novel group of dibenzo[b,f][1,4]-thiazepines, to methods of preparing such compounds; and to methods of employing them in the treatment and control of allergic conditions such as asthma.

In its composition aspect, therefore, the instant invention may be described as residing in the concept of isomeric dibenzo[b,f][1,4]thiazepines characterized by having the following structural formulae:

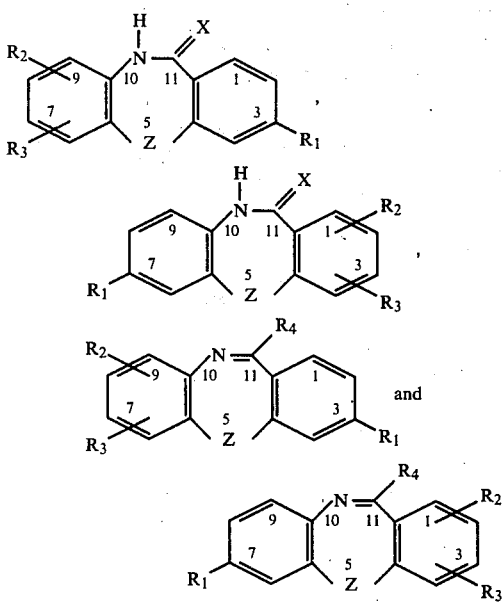

wherein
Z is a member selected from the group consisting of thio, sulfinyl, or sulfonyl;
X is a member selected from the group consisting of O and $H_2$;
$R_4$ is a member selected from the group consisting of hydrogen, morpholino and piperidino,
$R_2$ and $R_3$ are the same or different and are members selected from the group consisting of hydrogen, halogen, nitro, loweralkyl, amino, N-loweralkylamino, N,N-diloweralkylamino, loweralkanoyl, hydroxy, loweralkoxy, loweralkylthio, trifluoromethylthio, loweralkylsulfinyl, loweralkylsulfonyl and trifluoromethyl; and
$R_1$ is a member selected from the group consisting of 5-tetrazolyl, 5-tetrazolylmethyl, 3-hydroxy-1,2,5-thiazol-4-yl, 4-hydroxy-$\Delta^3$-pyrroline-3-yl-2,5-dione and

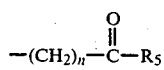

wherein
n is an integer from 0 to 4 and
$R_5$ is a member selected from the group consisting of hydroxy, loweralkoxy, N,N-diloweralkylaminoloweralkoxy, carboxyloweralkoxy, amino, N-loweralkylamino, N,N-diloweralkylamino, loweralkylsulfonylamino, carboxyloweralkylamino, carboxamidoloweralkylamino, and 2-imino-3-methylthiazolidine; and the pharmaceutically acceptable salts thereof.

As used herein, the term, halogen (or halo), includes chlorine, bromine, iodine and fluorine. Unless otherwise specifically stated, the terms, loweralkyl and loweralkoxy, include straight and branched chain alkyl and alkoxy groups having 1 to 4 carbon atoms in the alkyl or alkoxy moiety such as, for example, methyl, ethyl, n-propyl, isopropyl, n-butyl, methoxy, ethoxy, n-propoxy and isobutoxy. The term, loweralkanoyl, includes straight or branched chain alkanoyl groups having 1 to 4 carbon atoms in the alkanoyl moiety such as, for example, formyl, acetyl, propanoyl, isobutyryl and isobutyryl.

The instant invention is based upon applicant's discovery that the thiazepines of Formula I, IA, II and IIA, above, markedly antagonize the actions of contractile prostaglandins such as $PGF_2$, $PGG_2$, $PGH_2$ and $TXA_2$. The use of the thiazepines of this invention, which act as prostaglandin antagonists and biosynthetic inhibitors, offers a new approach to therapy in a variety of allergic conditions such as allergic asthma where excessive contractile activity of prostaglandins and prostaglandin biosynthetic intermediates occur. It is well known, for example, that prostaglandins such as $PGF_{2\alpha}$, $PGG_2$ $PGH_2$ and $TXA_2$, are potent contractants of bronchial muscle and that human asthmatics are especially sensitive to the bronchial constricting action of $PGF_{2\alpha}$. The antagonizing action of the thiazepines of this invention against the constricting actions of contractile prostaglandins has been confirmed in vitro and in vivo using standard pharmacological techniques. It is contemplated, therefore, that the thiazepines of this invention will be employed in dosage unit form as the essential active ingredient in pharmaceutical formulations intended for the treatment and control of allergic conditions such as asthma in humans and warm blooded animals.

The novel thiazepines of Formula I wherein Z is thio, X is oxygen and $R_1$ is carboxy are prepared by treating an appropriate $R_2$ and/or $R_3$-substituted o-aminothiophenol ($R_2$ and $R_3$ are as previously defined) with bromo terephthalic acid in a mixture of quinoline and pyridine in the presence of cuprous oxide. The reaction mixture is heated in an oil bath at 180° C. for 10 to 14 hours. Upon acidification, the 3-carboxylic acid separates and is recovered by filtration. Conveniently the acid is purified by esterification and hydrolysis by treating the crude acid with methanol in the presence of acetyl chloride and hydrolyzing the methyl ester so produced with aqueous sodium hydroxide. These reactions are summarized in the following general reaction scheme wherein $R_2$ and $R_3$ are as defined above:

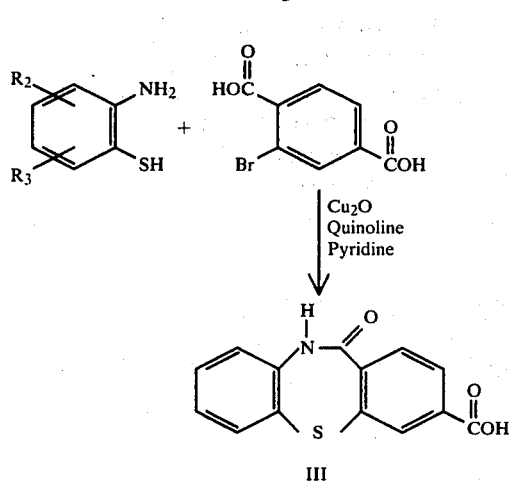

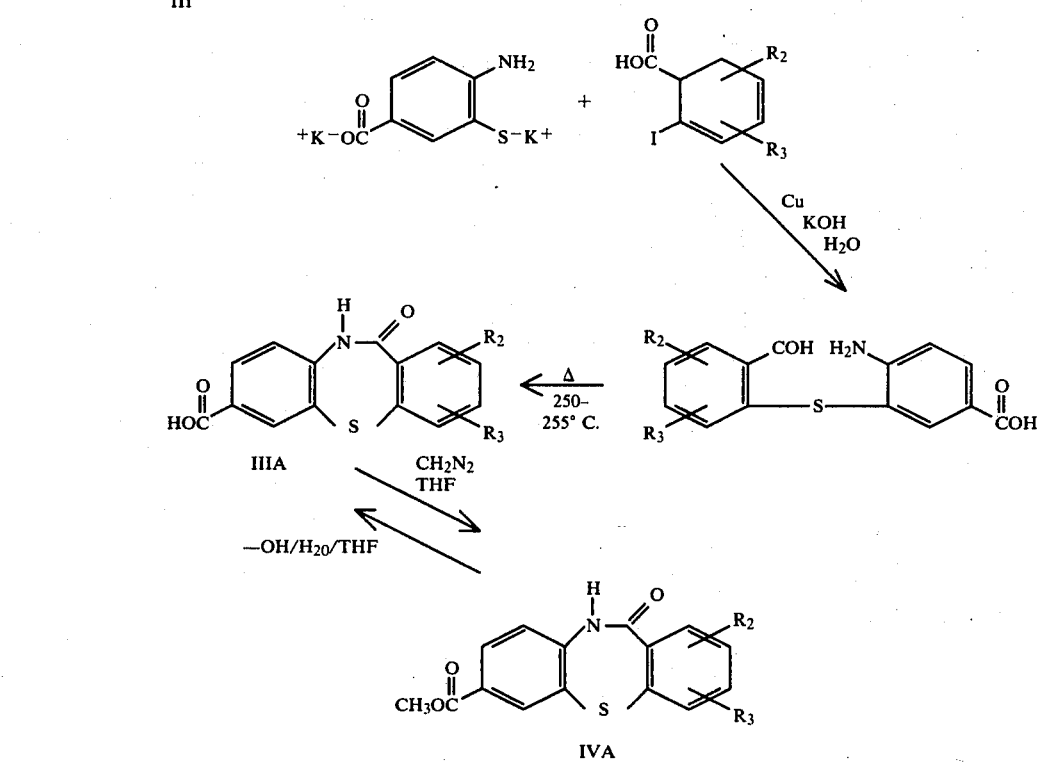

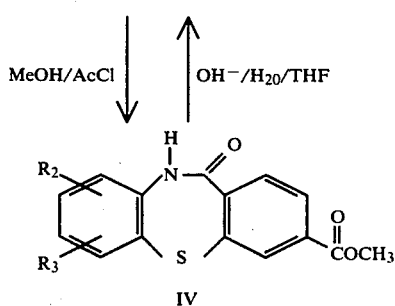

The novel thiazepines of Formula IA wherein Z is thio, X is oxygen and $R_1$ is carboxy are prepared by treating an appropriate $R_2$ and/or $R_3$-substituted o-iodobenzoic acid with the dipotassium salt of 4-amino-3-mercaptobenzoic acid. This reagent readily is prepared from 2-aminobenzothiazole-6-carboxylic acid (obtained by the procedure described in Ann., 558, pg. 29, 1947) by refluxing the thiazole in 50% aqueous potassium hydroxide for 2–4 hours. The cooled reaction mixture can be employed without further purification as the dipotassium salt. The iodobenzoic acid and dipotassium salt mixture is refluxed in the presence of copper metal powder for 1 to 3 hours to form the corresponding $R_2$ and/or $R_3$-substituted 4-amino-3-(o-carboxyphenylthio)-benzoic acid which then is heated dry to 250°–255° C., preferably under an inert atmosphere, for 1–3 hours to form the desired 10,11-dihydro-11-oxodibenzo[b,f][1,4]thiazepin-7-carboxylic acid. If desired, the acid can be esterified using diazomethane in tetrahydrofuran, for example, and hydrolyzed as an aid to purification. These reactions are illustrated in the following general reaction scheme wherein $R_2$ and $R_3$ are as defined above:

The novel thiazepines of Formula I and IA wherein Z is thio, X is $H_2$ and $R_1$ is carboxy conveniently are prepared by treating any desired $R_2$ and/or $R_3$-substituted methyl 10,11-dihydro-11-oxodibenzo[b,f][1,4]thiazepin-3(or 7)-carboxylate, a compound of Formula IV or IVA, with an equimolar mixture of phosphorous pentachloride in phosphorous oxychloride to form the corresponding methyl 11-chlorodibenzo[b,f][1,4]thiazepin 3(or 7)-carboxylate. The reaction is carried out at room temperature and usually requires 1 to 3 hours for completion. Additional phosphorous pentachloride may be added to speed the reaction and to insure complete conversion of the starting material. The 11-chloro ester then is treated with a reducing agent such as sodium borohydride to form the corresponding methyl 10,11-dihydrodibenzo[b,f][1,4]thiazepin-3(or 7)-carboxylate which is hydrolyzed with aqueous potassium hydroxide to form the desired 10,11-dihydrodibenzo[b,f][1,4]thiazepin-3(or 7)-carboxylic acid. These reactions are illustrated by the following reaction scheme wherein $R_2$ and $R_3$ are as previously defined:

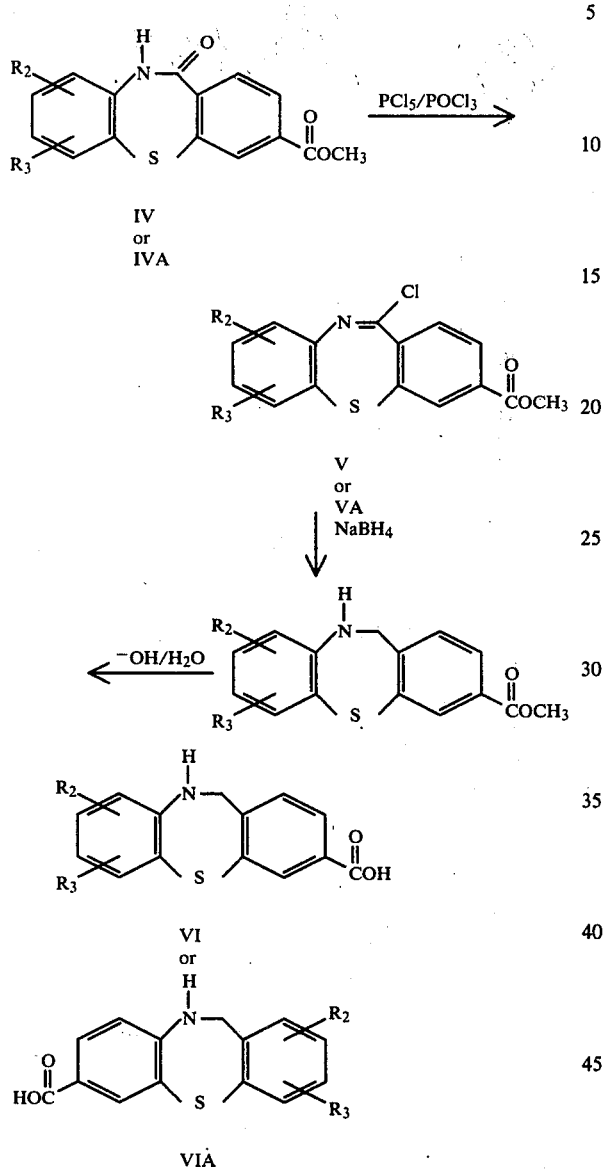

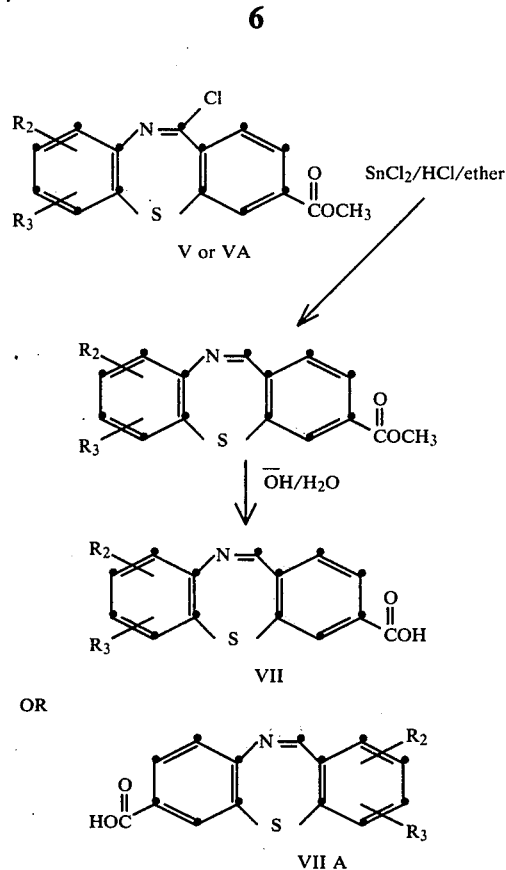

The novel thiazepines of Formula II and IIA wherein Z is thio, $R_4$ is hydrogen and $R_1$ is carboxy are prepared by treating any desired $R_2$ and/or $R_3$ substituted methyl 10,11-dihydrodibenzo[b,f][1,4]thiazepin-3(or 7)-carboxylate, a compound of Formula V or Va, with a solution of stannous chloride in ether which has been saturated with hydrogen chloride gas in order to obtain the corresponding methyl dibenzo[b,f][1,4]thiazepin-3(or 7)-carboxylate which is hydrolized with aqueous potassium hydroxide to form the desired dibenzo[b,f][1,4]thiazepin-3(or 7)-carboxylic acid. These reactions are illustrated by the following reaction scheme wherein $R_2$ and $R_3$ are previously defined:

The novel thiazepines of Formula II and IIA wherein Z is thio, $R_4$ is morpholino and $R_1$ is carboxy are prepared by treating any desired $R_2$ and/or $R_3$ substituted methyl 11-chlorodibenzo[b,f][1,4]thiazepin-3(or 7)-carboxylate, a compound of formula V or VA, with morpholine in order to form the corresponding methyl 11-morpholinodibenzo[b,f][1,4]thiazepin-3(or 7)-carboxylate. The reaction usually is carried out at reflux under an inert atmosphere, argon for example, and usually requires from 36 to 48 hours for completion. The 11-morpholino methyl carboxylate so produced then may be hydrolized with aqueous potassium hydroxide to form the desired 11-morpholinodibenzo[b,f][1,4]-thiazepin-3(or 7)-carboxylic acid. Where the 11-piperidino derivative is desired, it is necessary only to substitute pyridine for morpholine in the reactions described above. These reactions are illustrated by the following reaction scheme wherein $R_2$ and $R_3$ are as previously defined:

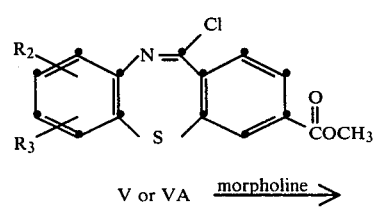

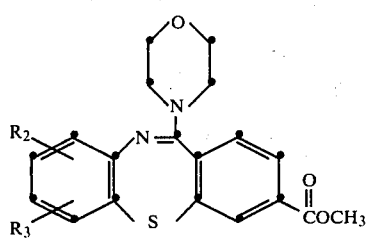

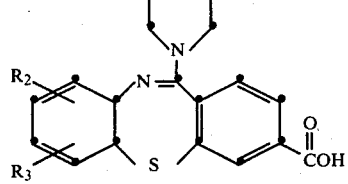

VIII or

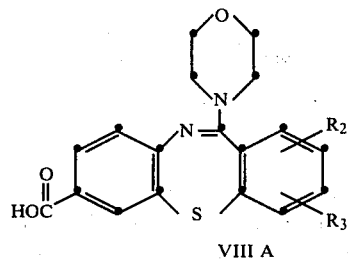

VIII A

Formation of the 11-oxide or the 11,11-dioxide groups (e.g., preparation of the sulfinyl or sulfonyl compounds of the instant invention) conveniently is achieved by controlled oxidation techniques. Thus, for example, the 3-(or 7)-carboxylic acid derivatives of formula III or IIIA, or the corresponding 3-(or 7)-loweralkyl carboxylates, may be oxidized with hydrogen peroxide in the presence of an acidic solvent such as acetic acid or with organic peroxides such as peroxy acid, for example, m-chloroperbenzoic acid and the like, in a stepwise fashion to form the corresponding sulfinyl derivative, formula IX or IXA, and sulfonyl derivative, formula X or XA, by controlling the molar ratio of oxidant to reductant. The molar ratio determines the oxidation level of the sulfur in the product. A 1:1 molar ratio, for example, results largely in the production of the sulfinyl derivative whereas a 2 to 3 molar excess of oxidant results in a yield predominantly comprising the sulfonyl derivatives.

III

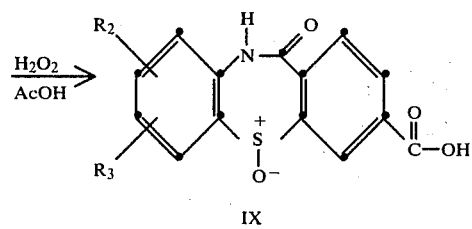

IX

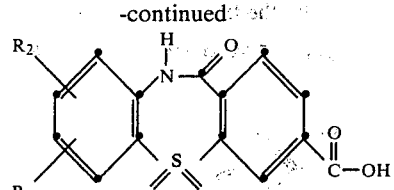

X

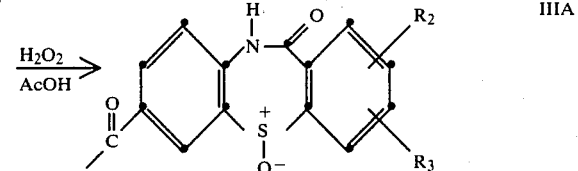

IX A

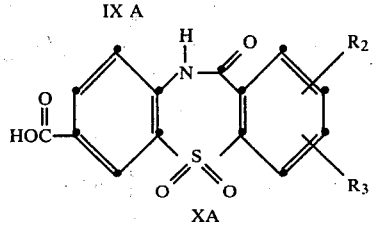

XA

The oxidation technique described above is generally applicable to preparation of any of the sulfinyl or sulfonyl compounds of this invention from the corresponding thiazepin. Thus, for example, the 3-(or 7)-carboxylic acid compounds of formula VI or VIA, VII or VIIA and VIII or VIIIA, or the corresponding 3-(or 7)-loweralkyl carboxylates, may be subjected to controlled oxidation in order to obtain the corresponding sulfinyl and sulfonyl compounds.

In addition to their therapeutic properties as noted above, the 3-(or 7)-carboxylic acid derivatives of this invention serve as valuable intermediates in the preparation of other variously substituted dibenzo[b,f][1,4]-thiazepines of Formula I, IA, II and IIA. Thus, for example, the 3-(or 7)-carboxylic acid of formula III or IIIA may be converted readily into the corresponding acid halide, preferably the acid chloride, by treating the carboxylic acid with a thionyl halide, preferably thionyl chloride. The resulting 3-(or 7)-halocarbonyl-10,11-dihydro-11-oxodibenzo[b,f][1,4]-thiazepine (i.e., the 3-(or 7)-chlorocarbonyl compounds of formula XI or XIA then may be treated with various well-known reagents to form desired ester and amide derivatives. These reactions are illustrated in the following reaction scheme wherein $R_2$ and $R_3$ are as previously defined, it being understood that they are equally applicable to the 3-(or 7)-carboxylic acids of formula VI or VIA, VII or VIIA and VIII or VIIIA.

III
III A ⎯SOCl₂⟶

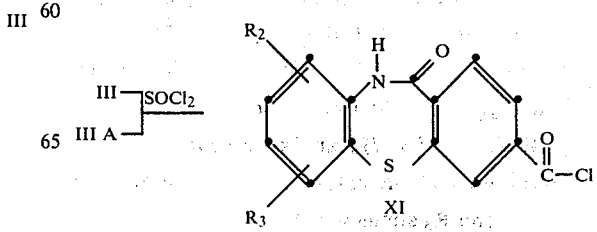

XI

-continued

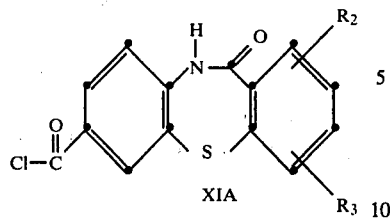

XIA

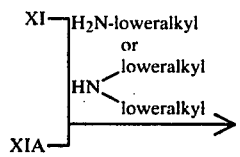

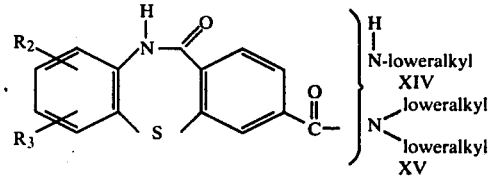

Thus, for example, the chlorocarbonyl compounds of formula XI and XIA may be treated:

(a) with a loweralkanol such as, for example, methanol, ethanol, 2-propanol, butanol and 2-butanol, to form the corresponding loweralkyl esters, XII and XIIA:

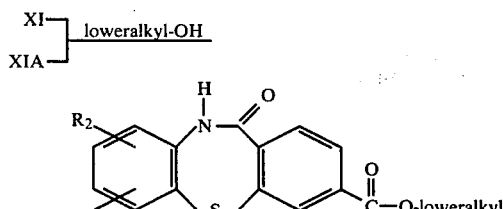

XII

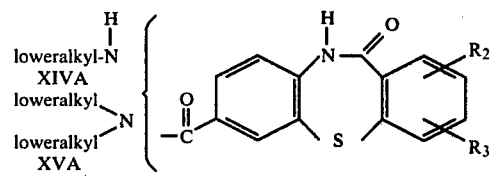

XIIA (b) with ammonia to form the corresponding carboxamide, XIII and XIIIA:

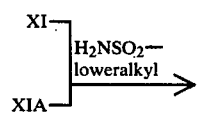

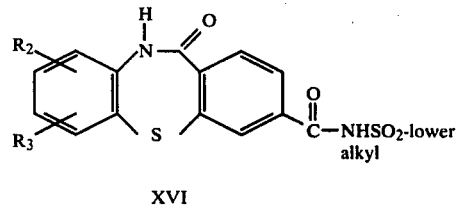

XIII

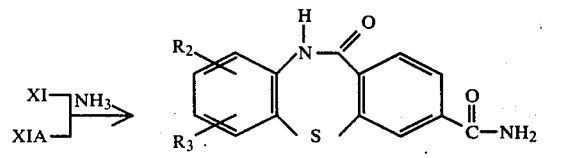

XIIIA (c) with an N-loweralkylamine such as, for example, methylamine, ethylamine, propylamine, isopropylamine and butylamine, or an N,N-diloweralkylamine such as, for example, dimethylamine, diethylamine, dipropylamine and dibutylamine, to form the corresponding N-loweralkylcarboxamide XIV or XIVA or N,N-diloweralkylcarboamide, XV or XVA:

(d) with a loweralkylsulphonamide such as, for example, methanesulphonamide, ethanesulphonamide, propanesulphonamide and butanesulphonamide, to form the corresponding N-loweralkylsulfonylcarboxamide, XVI or XVIA:

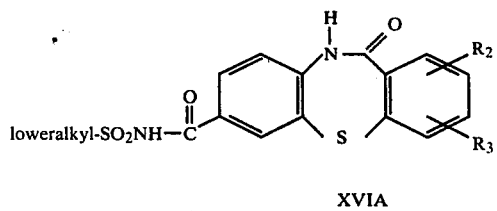

XVI

XVIA (e) with 2-imino-3-methylthiazolidine to form the corresponding (3-methyl-2-thiazolidinylidene)carboxamide, XVII and XVIIA:

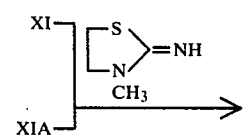

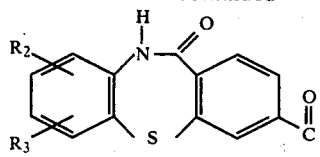

XVII

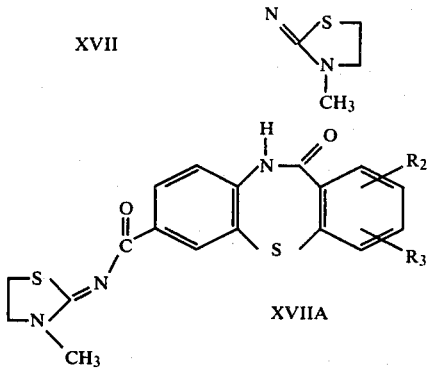

XVIIA (f) with a loweralkyldiol such as, for example ethylene glycol, trimethylene glycol and 1,4-butanediol, to form the corresponding hydroxyloweralkylester, XVIII and XVIIIA:

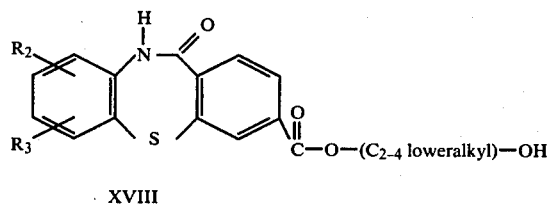

XVIII

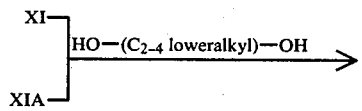

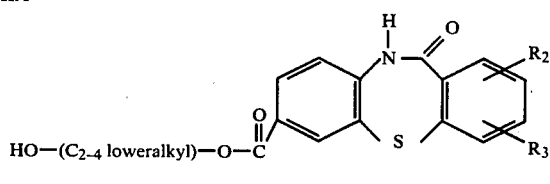

XVIIIA (g) with an N,N-diloweralkylaminoloweralkanol such as, for example, N,N-dimethylethanolamine, N,N-diethylethanolamine, 3-N,N-dimethylaminopropan-1-ol and 4-N,N-diethylaminobutan-1-ol, to form the corresponding N,N-diloweralkylaminoloweralkyl ester, XXI and XXIA:

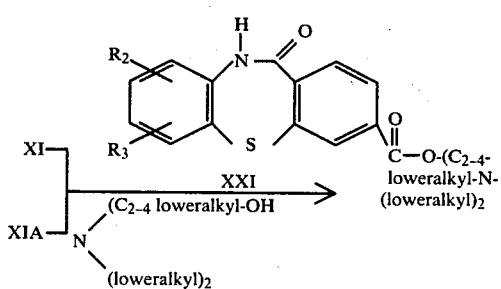

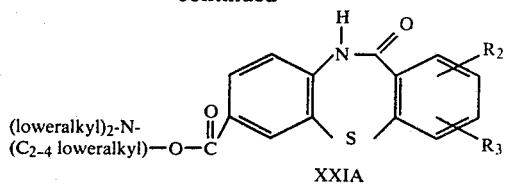

XXIA (h) with an amino acid such as, for example, glycine, alanine and valine, to form the corresponding N-carboxyloweralkylcarboxamide, XXII and XXIIA:

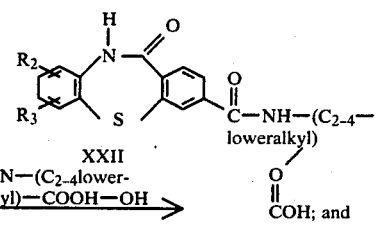

XXII

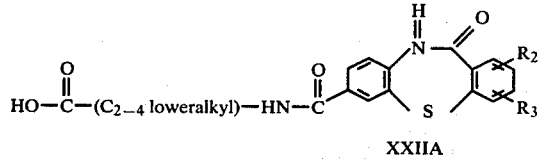

XXIIA (i) with an alkali metal salt of a hydroxyloweralkanoic acid such as, for example, hydroxyacetic acid, 3-hydroxybutyric acid and β-hydroxypropionic acid, to form the corresponding carboxyloweralkyl ester, XXIII and XXIIIA:

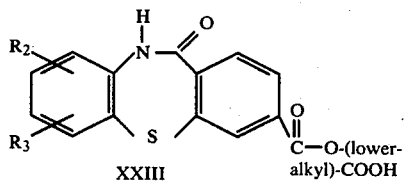

XXIII

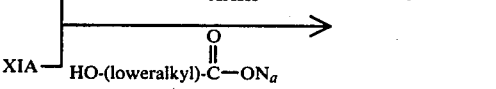

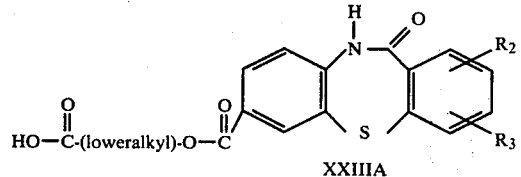

XXIIIA

Where the corresponding sulfinyl or sulfonyl derivatives are desired, the corresponding 11-oxide or 11,11-dioxide 3-(or 7)-carboxylic acid, a compound of Formula IX, IXA, X or XA, for example, may be substituted for starting material IV or IVA in the foregoing reaction sequence. Alternatively, it will be clear to those skilled in the art that the product esters and amides obtained in the foregoing reaction sequence may be oxidized by the techniques already described to obtain the corresponding sulfinyl or sulfonyl derivatives.

Those thiazepines of this invention wherein the substituent at the 3-(or 7)-position is 3-hydroxy-1,2,5-thiadiazol-4-yl are prepared by refluxing a 3-(or 7)- cyano intermediate (a compound of Formula XXIV or XXIVA, for example, prepared as hereinafter described) in formic acid in the presence of Raney nickel alloy for 1 to 2 hours in order to obtain the corresponding 10,11-dihydro-11-oxodibenzo-[b,f][1,4]thiazepin-3-(or 7)-carboxaldehyde. The aldehyde product then is converted into the corresponding 3-(or 7)-(2-aminoacetonitrile) by treatment with sodium cyanide in an alcoholic solvent saturated with ammonia and in the presence of ammonium chloride and ammonium hydroxide. The reaction usually is conducted at room temperature and requires from 8 to 16 hours for completion. The aminoacetonitrile so produced is treated with concentrated hydrochloric acid at room temperature for 20 to 45 minutes in order to obtain the corresponding 3-(or 7)-(2-aminoacetamide) which then is treated with sulfur monochloride in dimethylformamide to obtain the desired 3-(or 7)-(3-hydroxy-1,2,5-thiadiazol-4-yl)-10,11-dihydro-11-oxo-dibenzo[b,e][1,4]thiazepin of Formula XXV and XXVA. This reaction sequence is illustrated in the following diagram, it being understood that position of the 3-hydroxy-1,2,5-thiadiazol-4-yl substituent in the final product depends upon the selection of the appropriate 3-(or 7)-cyano starting material.

The 3-(or 7)-cyano intermediate, the compound of formula XXIV or XXIVA, employed as the starting material in the foregoing reaction scheme, is readily prepared by treating a 3-(or 7)-loweralkyl ester, preferably the methyl ester, derived from a 3-(or 7)-carboxylic acid of formula I, IA, II or IIA by techniques already described, in methanol saturated with ammonia gas for 18 to 36 hours at room temperature. The crude amide obtained after evaporation of the reaction mixture then is refluxed in ethylene chloride containing phosphorus oxychloride for 6 to 10 hours. The reaction mixture is diluted with water and the organic phase is separated and dried to obtain the cyano product. This reaction is illustrated in the following diagram, it being understood that the position of the 3-cyano group in the final product depends upon the selection of the appropriate 3-(or 7)-loweralkyl ester starting material.

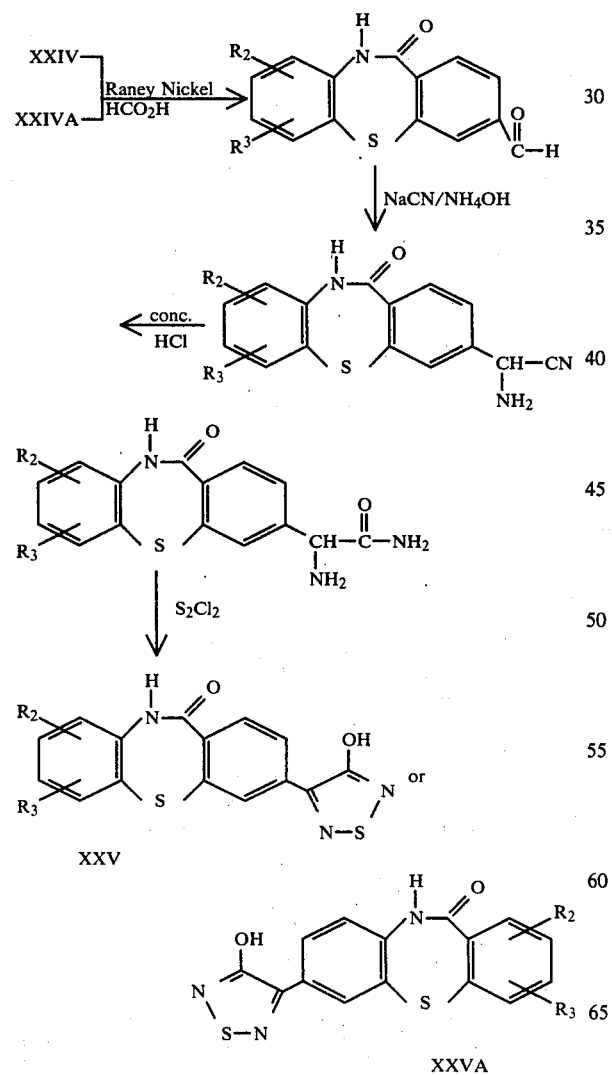

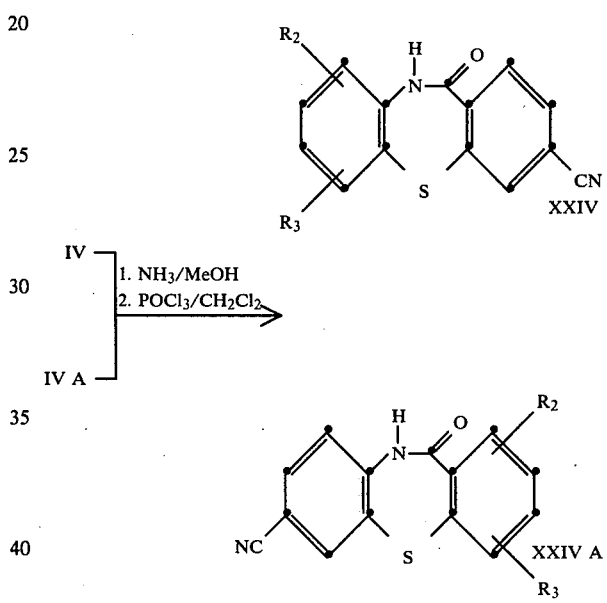

The novel thiazepines of this invention wherein the substituent at the 3-(or 7)-position is 5-tetrazolyl also are prepared from the 3-(or 7)cyano intermediates of formula I, IA, II and IIA. The nitrile of formula XXIV or XXIVA, for example, is heated in a mixture of sodium azide and ammonium chloride in a suitable organic solvent such as dimethylformamide. Conveniently, the reaction is carried out at reflux and usually requires 4 to 12 hours for completion. After dilution with excess sodium carbonate and extraction with ethyl acetate, the aqueous phase is acidified to obtain the desired 3-(or 7)-(1H-tetrazol-5-yl)-10,11-dihydro-11-oxodibenzo[b,f][1,4]thiazepine of formula XXVI or XXVIA. The reaction is illustrated in the following reaction scheme wherein $R_2$ and $R_3$ are as defined above.

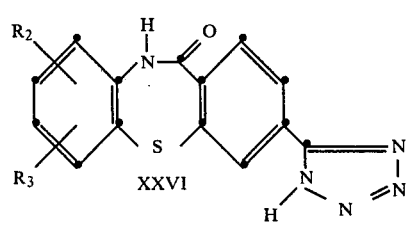

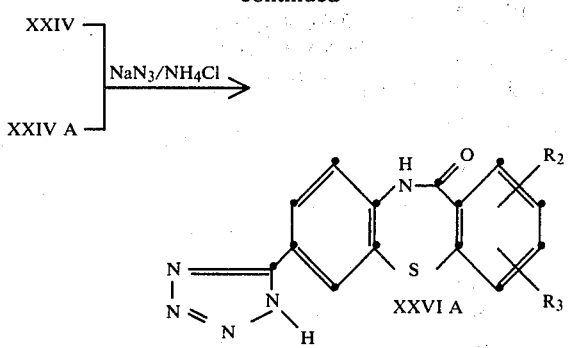

The novel thiazepines of this invention wherein the substituent at the 3-(or 7)-position is 4-hydroxy-Δ³-pyrroline-3-yl-2,5-dione are prepared from the appropriately substituted 3-(or 7)-carboxylic acid by reducing the acid to the corresponding alcohol with borane in tetrahydrofuran. The reaction conveniently is carried out at room temperature under an inert atmosphere and usually requires 2 to 4 hours for completion. The alcohol then is brominated with phosphorus tribromide and the bromomethyl compound so produced is treated with sodium cyanide to form the corresponding 3-(or 7)-cyanomethyl derivative. These reactions may be carried out at room temperature and usually require from 1 to 3 hours for completion. The cyanomethyl intermediate then is hydrolyzed to the corresponding acetic acid which is treated with thionyl chloride followed by ammonia to form the corresponding 3-(or 7)-acetamide derivative by techniques already described. The acetamide then is treated with diethyl oxalate in dimethylformamide in the presence of potassium t-butoxide to form the desired 3-(or 7)-(4-hydroxy-Δ³-yl-2,5-dione)-dibenzo-[b,e][1,4]thiazepine, XXVII or XXVIIA.

This reaction sequence is illustrated in the diagram below, it again being understood that the position of the hydroxypyrrolindione in the final product depends upon the selection of the 3-(or 7)-carboxylic acid starting material.

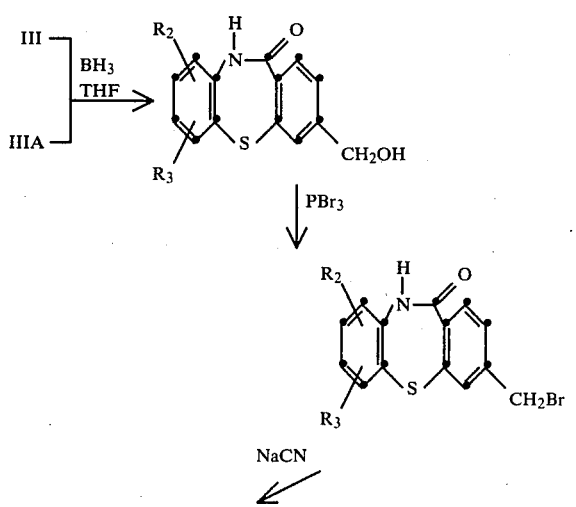

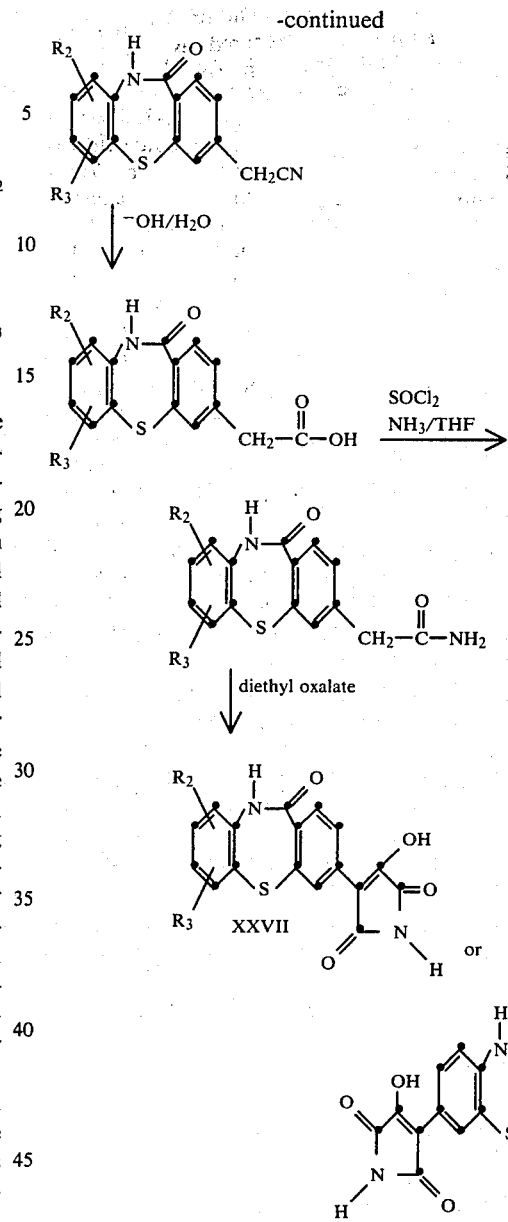

Where corresponding sulfinyl or sulfonyl derivatives are desired, the products of the four reaction schemes described immediately above may be oxidized by the techniques already described.

It will be noted that the reaction sequence described above affords not only thiazepines of this invention wherein the substituent at the 3-(or 7)-position is 4-hydroxy-Δ³-pyrroline-3-yl-2,5-dione, but, in Steps A–D, leads also to the preparation of those thiazepines of this invention wherein the substituent at the 3-(or 7)-position is a loweralkanoic acid (i.e. compounds of Formula I, IA, II, and IIA wherein $R_1$ is

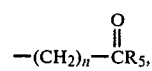

n is an integer between 1 and 4 and $R_5$ is hydroxy). Thus, Steps A–D, as described above, starting with the appropriately substituted 3-(or 7)-carboxylic acid, through reduction, bromination, cyanization and oxidation, affords the corresponding 3-(or 7) acetic acid derivative. Quite obviously, the described reduction, bromination, cyanization and oxidation sequence can be repeated, employing the 3-(or 7)-acetic acid derivative as starting material, in order to obtain the corresponding propionic acid derivative which, in turn, can be employed as starting material for preparing the corresponding butyric acid derivative. In this manner, any desired 3-(or 7)-loweralkanoic acid derivative of the instant invention readily is prepared. Corresponding sulfinyl or sulfonyl derivatives are prepared by the oxidation techniques previously described.

The 3-(or 7)-cyanoloweralkyl intermediates obtained from Steps A–C in the reaction sequence described above also serve as intermediates in the preparation of other therapeutically active thiazepines of Formula I, IA, II and IIA. Thus, for example, an appropriately substituted 3-(or 7)-cyanomethyl-10,11-dihydro-11-oxodibenzo[b,f][1,4]-thiazepine may be treated with sodium azide and ammonium by techniques previously described to form the corresponding 3-(or 7)-(1H-tetrazol-5-ylmethyl)-10,11-dihydro-11-oxodibenzo[b,f][1,4]thiazepine and the product, if desired, can be oxidized to form the corresponding sulfinyl or sulfonyl derivative.

As noted above, pharmaceutically acceptable salts of the novel thiazepines also are included within the scope of this invention. The term, pharmaceutically acceptable salts, is intended to include salts derived from pharmaceutically acceptable non-toxic acids and bases such as, for example, ammonium salts, alkali metal salts such as sodium and potassium salts, alkaline earth metal salts such as magnesium and calcium salts, salts of organic bases such as amine salts derived from mono-, di and tri-loweralkyl or loweralkanoyl amines such as trimethylamine, dimethylamine and triethanolamine, salts derived from heterocyclic amines such as piperidine, piperazine and morpholine, and salts derived from pharmaceutically acceptable acids such as hydrochloric acid, sulfuric acid, tartaric acid and propionic acid.

The thiazepines of Formula I, IA, II and IIA are useful in the treatment and prophylaxis of human or warm-blooded animal disease conditions where excessive undesirable contractile activity of prostaglandins, such as $PGF_{2\alpha}$, or prostaglandin biosynthetic intermediates contribute. In particular, they are of value in the treatment and control of allergic conditions such as asthma.

The magnitude of a prophylactic or therapeutic dose of compound of Formula I, IA, II and IIA will, of course, vary with the nature and the severity of the condition to be treated and with the particular compound of Formula I, IA, II and IIA and its route of administration. In general, the dose range lies within the range of 0.2 mg. to 100 mg. per kg. body weight per day.

The pharmaceutical compositions of the present invention comprise a compound of Formula I, IA, II and IIA as an active ingredient, and may also contain pharmaceutically acceptable carrier and optionally other therapeutic ingredients. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the condition being treated and on the nature of the active ingredient. They may be conveniently presented in unit dosage form and prepared by any of the methods well known in the art of pharmacy.

For use where a composition for intravenous administration is employed, a suitable dosage range is from 0.2 to 20 mg. (preferably 1 to 15 mg.) of a compound of Formula I, IA, II and IIA per kg. of body weight per day and in the case where an oral composition is employed a suitable dosage range is about, e.g., 1 to 50 mg. of a compound of formula I, IA, II and IIA per kg. of body weight per day, preferably from 10 to 40 mg./kg.

Pharmaceutical compositions of the present invention suitable for oral administration and by inhalation in the case of asthma therapy may be presented as discrete units such as capsules, cachets or tablets each containing a predetermined amount of the active ingredient; as a powder or granules; or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of powdered compound moistened with an inert liquid diluent. Desirably, each tablet contains from 50 mg. to 500 mg. of the active ingredient and each cachet or capsule contains from 50 mg. to 500 mg. of the active ingredient.

The best mode contemplated by applicants for carrying out their invention is illustrated in the following working examples. No limitation, however, is intended except as set forth in the appended claims.

EXAMPLE 1

10,11-Dichloro-11-oxodibenzo[b,f][1,4]thiazepin-3-carboxylic Acid

Heat a mixture of 15.7 gm (0.1256 mole) of o-aminothiophenol, 15.4 gm (0.0629 mole) of bromoterephthalic acid. 4.98 gm (0.0346 mole) of cuprous oxide, 63 ml of quinoline and 6.3 ml of pyridine in an oil bath at 180° C. overnight. Cool to room temperature, add 200 ml of concentrated hydrochloric acid and stir for 30 minutes. Separate the solids by filtration and wash well with water. Dissolve the solids in hot tetrahydrofuran and filter. Treat the filtrate with charcoal, filter and strip the filtrate to dryness to obtain the title product.

EXAMPLE 2

Methyl 10,11-Dihydro-11-oxodibenzo[b,f][1,4]thiazepin-3-carboxylate

Add 4 gm of the thiazepin-3-carboxylic acid of Example 1, to a mixture of 5 cc of acetyl chloride in 300 cc of methanol and stir the mixture at room temperature for 48 hours. Strip the reaction mixture to dryness and chromatograph the residue over silica gel eluting with 20% ethyl acetate in benzene to obtain the title product (m.p. 255°–257° C.).

EXAMPLE 3

10,11-Dihydro-11-oxodibenzo[b,f][1,4]thiazepin-3-carboxylic Acid

Dissolve 1.49 gm of the ester of Example 2 in 50 cc of tetrahydrofuran. Add 40 cc of 10% sodium hydroxide and stir at room temperature for 3 hours. Evaporate the tetrahydrofuran and extract the aqueous residue with ethyl acetate. Acidify and separate the precipitate by filtration. Wash the precipitate well with water and dry in vacuo to obtain the title product (m.p. 362°–364° C.).

EXAMPLE 4

10,11-Dihydro-11-oxodibenzo[b,f][1,4]thiazepin-3-carboxylic Acid 5-Oxide

Step A: Methyl 10,11-Dihydro-11-oxodibenzo[b,f][1,4]thiazepin-3-carboxylate 5-Oxide Dissolve 2 gm (0.0071 moles) of the ester of Example 2 in 200 cc of chloroform and 1.396 gm of m-chloroperbenzoic acid and stir at room temperature for 20 minutes. Add successive 100 mg portions of m-chloroperbenzoic acid until thin layer chromatography slows conversion of the starting material. Basify with calcium hydroxide and separate the solids. Chromotograph the solids over silica gel eluting with 30% ethyl acetate in benzene to obtain the title product (yield 870 mg).

Step B: 10,11-Dihydro-11-oxodibenzo[b,f][1,4thiazepin-3-carboxylic Acid 5-Oxide

Stir the oxide from Step A in a mixture of 5 cc of aqueous sodium hydroxide and 10 cc of tetrahydrofuran for 15 minutes. Evaporate the tetrahydrofuran, dilute with water. Filter and acidify the filtrate. Separate the solids by filtration and dry in vacuo at 50° C. Suspend the product in water. Stir overnight, filter and dry at 60° C. to obtain the title product (Yield 605 mg).

Analysis: Calculated for $C_{14}H_9NO_4S$-C: 58.54. H: 3.13, N: 4.87 S: 11.15: Found: C: 58.46, H: 3.41, N: 4.78 S: 11.04.

EXAMPLE 5

10,11-Dihydro-11-oxodibenzo[b,f][1,4]thiazepin-3-carboxylic Acid 5,5-Dioxide

Step A: Methyl 10,11-Dihydro-11-oxo-dibenzo[b,f][1,4]thiazepin-3-carboxylate 5,5-Dioxide Dissolve 570 mg (2 mmoles) of the ester of Example 2 in a mixture of 2.3 gm of m-chloroperbenzoic acid and 75 cc of chloroform and stir for 12 hours at room temperature. Basify with calcium hydroxide. Filter and evaporate to dryness. Chromatograph the residue over silica gel eluding with 30% ethyl acetate in benzene. Collect the sulfone fractions and evaporate to dryness. Stir the residue in ether for 30 minutes, filter and dry to obtain the title product (m.p. 300°–302° C.), sintered around 295° C.).

Step B: 10,11-Dihydro-11-oxo[b,f][1,4]thiazepin-3-carboxylic acid 5,5-Dioxide

Dissolve 200 mg of the sulfane from Step A in a mixture of 5 cc of 10% aqueous sodium hydroxide and 10 cc of tetrahydrofuran and stir at room temperature for 15 minutes. Evaporate the tetrahydrofuran, dilute with water and filter. Acidify with hydrochloric acid and separate the solids by filtration. Stir the solids in ether for 20 minutes, filter and dry to obtain the title product, (m.p. over 360° C.)°.

EXAMPLE 6

Methyl 11-chlorodibenzo[b,f][1,4]thiazepin-3-carboxylate

At room temperature, add 14.25 gm. (50 mmole) of methyl 10,11-dihydrodibenzo[b,f][1,4]-thiazepin-11-one-3-carboxylate to a stirred mixture of 10.425 gm. (50 mmole) of phosphorous pentachloride in 50 ml. of phosphorous oxychloride. Stir for 30 minutes, add an additional 1 gm. of phosphorous pentachloride and continue stirring for one hour. Partition the reaction mixture between a mixture of 400 ml. of methylene chloride, 350 gm. of ice and 150 ml. of water. Separate the aqueous layer and extract with 50 ml. of methylene chloride. Wash the combined organic extracts with a mixture of 100 gm. of ice and 100 ml. of water. Dry the methylene chloride solution over magnesium sulfate, charcoal and filter. Evaporate the solution, take-up in 50 ml. of dry toluene and again evaporate. Take up the residue in 25 ml. of acetonitrile, cool in an ice bath and separate the precipitate by filtration to obtain the title product. (m.p. 134°–135.5° C.)

EXAMPLE 7

Methyl 10,11-dihydrodibenzo[b,f][1,4]thiazepin-3-carboxylate

Suspend 3.035 gm. (10 mmole) of methyl 11-chlorodibenzo[b,f][1,4]thiazepin-3-carboxylate in 30 ml. of solfolane (tetrahydrothiophene 1,1-dioxide) and add 766 mg. (20 mmole) of sodium borohydride in small portions with stirring. Stir at room temperature for 3 hours, add a further 190 mg. (5 mmole) of sodium borohydride and continue stirring for 1 hour. Pour the reaction mixture into 100 ml. of ice-water. Extract with three 50 ml. portions of dry ether. Wash the ether extract twice with 50 ml. portions of saturated aqueous sodium chloride, dry over magnesium sulfate and evaporate to a residue. Chromatograph the residue over 100 gm. of silica gel eluting with 1:9 ethyl acetate in toluene. Recrystallize the recovered product from acetonitrile to obtain the title product. (m.p. 149°–150° C.).

EXAMPLE 8

10,11-dihydrodibenzo[b,f][1,4]thiazepin-3-carboxylic Acid

Stir a mixture of 136 mg. (0.5 mmole) of the ester of Example 7, 65.9 mg. (1 mmole) of 85% aqueous potassium hydroxide, 0.65 ml. of water, 3.25 ml. of ethanol, and 0.325 ml. of dioxane under argon at room temperature for 12 hours. Evaporate the mixture to dryness. Dissolve the residue in water and acidify with acetic acid. Recover the precipitate by filtration and wash with water. Dry in vacuo over calcium chloride and

EXAMPLE 9

Methyl Dibenzo[b,f][1,4]thiazepin-3-carboxylate

Stir at room temperature a mixture of 4.27 gm. (22.54 mmole) of stannous chloride in 200 ml. of dry ether while passing dry hydrogen chloride through the mixture to saturation. Dissolve 3.42 gm. (11.27 mmole) of the 11-chloro ester of Example 6 in 35 ml. of methylene chloride and add this solution to the stannous chloride solution over a 10 minute period. Pass dry hydrogen chloride through the mixture for 30 minutes and decant the supernatant liquid. Wash the residue by decantation with dry ether. Filter and wash with dry ether. Shake the solids for 2 minutes in a mixture of 25 ml. of 5 N aqueous sodium hydroxide and 25 ml. of methylene chloride. Separate the organic layer and extract the aqueous layer with 25 ml. of methylene chloride. Wash the combined extracts with water, separate the organic layer and dry over magnesium sulfate. Evaporate to a residue. Recrystallize from acetonitrile to obtain the title product, (m.p. 103.5°–109.5° C.).

EXAMPLE 10

Dibenzo[b,f][1,4]thiazepin-3-carboxylic Acid

Add 269 mg. (1 mmole) of the ester of Example 9 to a solution of 132 mg. (2 mmole) of 85% aqueous potassium hydroxide in a mixture of 6.5 ml. of ethanol, 0.65 ml. of dioxane and 1.3 ml. of water. Stir at room temperature for 2 hours. Filter and evaporate the solution to a small volume. Dilute with 9 ml. of water and acidify with acetic acid. Filter wash the solids with water and dry. Dissolve the product in 9 ml. of hot tetrahydrofuran, filter and dilute with 9 ml. of methanol. Evaporate to a thick slurry, dilute with 2 ml. of methanol, filter and wash with methanol. Dry to obtain the title product, (m.p. sinters 289° C., m.p. 290°–291° C. dec.).

EXAMPLE 11

Methyl 11-Morpholinodibenzo[b,f][1,4]thiazepin-3-carboxylate

Reflux a mixture of 3.035 gm. (10 mmole) of the 11-chloro ester of Example 6, 2.61 mg. (30 mmmole) of morpholine and 30 ml. of dry acetonitrile under an argon atmosphere for 40 hours. Add 50 ml. of ice-water to the reaction mixture and extract twice with 50 ml. portions of ethyl acetate. Wash the combined extracts with 50 ml. of water and then with 50 ml. of saturated aqueous sodium chloride solution. Dry over magnesium sulfate and evaporate. Chromatograph the residue over silica gel eluting with 1:9 ethyl acetate in toluene. Recrystallize from diisopropyl ether to obtain the title product, (m.p. 114°–115° C.).

EXAMPLE 12

11-Morpholinodibenzo[b,f][1,4]thiazepin-3-carboxylic Acid

Stir a mixture of 1.77 gm. (5 mmole) of the ester of Example 11, 1.12 gm. (10 mmole) of 85% aqueous potassium hydroxide, 5.5 ml. of water, 27.5 ml. of ethanol and 2.75 ml. of dioxane under argon at room temperature for 2½ hours. Evaporate to a small volume and dilute with 18 ml. of water. Filter and acidify with acetic acid to pH 4.5. Separate the precipitate by filtration, wash with water and dry in vacuo over calcium chloride. Recrystallize from acetonitrile to obtain the title product, (m.p. 267°–269° C.).

EXAMPLE 13

11-Piperidinodibenzo[b,f][1,4]thiazepin-3-carboxylic Acid

Repeat the process of Examples 11 and 12, substituting an equivalent quantity of piperidine for the morpholine employed in Example 11, in order to obtain the title product.

EXAMPLE 14

Methyl 11-Chlorodibenzo[b,f][1,4]thiazepin-3-carboxylate 5,5-Dioxide

Add 6.34 gm. (20 mmole) of finely powdered methyl 10,11-dihydro-11-oxodibenzo[b,f][1,4]thiazepin-3-carboxylate 5,5-dioxide to a mixture of 6.25 gm. (30 mmole) phosphorous pentachloride in 17.3 ml. of phosphoryl chloride. Stir for 18 hours at room temperature. Separate the solids by filtration, wash with ether and dry in vacuo over potassium hydroxide. Dissolve the crude product in boiling tetrahydrofuran, filter and evaporate to a small volume in a stream of nitrogen. Dilute with acetonitrile and separate the precipitate by filtration in order to obtain the title product. (m.p. 254°–256° C.).

EXAMPLE 15

Methyl 10,11-dihydrodibenzo[b,f][1,4]thiazepin-3-carboxylate 5,5-Dioxide

Suspend 6.7 gm. (20 mmole) of methyl 11-chlorodibenzo[b,f][1,4]thiazepin-3-carboxylate 5,5-dioxide in 60 ml. of sulfolane and stir under nitrogen at room temperature while adding 1.52 g. (40 mmole) of sodium borohydride in small portions. Control foaming, if desired, by adding small portions of dry ether. After 2 hours, pour the reaction mixture into 300 ml. of ice-water and 75 ml. of ether. Separate the precipitate by filtration, wash with water and dry in vacuo. Dissolve the precipitate in 175 ml. of boiling acetonitrile, filter and concentrate to 100 ml. Separate the precipitate to obtain the title product. (m.p. 236° C.)

EXAMPLE 16

10,11-Dihydrodibenzo[b,f][1,4]thiazepin-3-carboxylic Acid 5,5-Dioxide

Stir a mixture of 3.03 gm. (10 mmole) of the ester of Example 15, 2.24 gm. (20 mmole) of 85% aqueous potassium hydroxide, 11 ml. of water, 55 ml. of ethanol and 5.5 ml. of dioxane under nitrogen for 2 hours. Concentrate the reaction mixture to the point of crystallization and dilute with 40 ml. of water. Filter and acidify with acetic acid. Separate the precipitate by filtration and wash with water and dry to obtain the title product (m.p. 304°–306° C.).

EXAMPLE 17

Methyl Dibenzo[b,f][1,4]thiazepin-3-carboxylate 5,5-Dioxide

Stir a suspension of 12.766 gm (67.33 mmole) of anhydrous stannous chloride in 350 ml of dry ether while passing dry hydrogen chloride through the suspension at a rate sufficient to cause brisk reflut. When the suspension is saturated, add 5.63 gm 16,83 mmole) of methyl-11-chlorodibenzo[b,f][1,4]thiazepin-3-carboxylate 5,5-dioxide in portions over 15 minutes. Continue introduction of hydrogen chloride for 1 hour. Decant the ether layer and pour the residue into a mixture of 200 ml of ether and 100 ml of water. Separate the ether layer and wash with 25 ml of 5 N aqueous sodium hydroxide and then with 50 ml of saturated sodium chloride solution. Dry the ether layer over magnesium sulfate and evaporate to 20 ml. Separate the precipitate by filtration. Chromatograph over silica gel eluting with 1:4 ethyl acetate in toluene. Dissolve the product in boiling methanol, filter and evaporate to 10 ml. Separate the solid by filtration to obtain the title product (m.p. 181°–181.5° C.).

EXAMPLE 18

Dibenzo[b,f][1,4]thiazepin-3-carboxylic Acid 5,5-Dioxide

Stir a mixture 2.04 gm (6.77 mmole) of the ester from Example 17. 2.24 gm (20 mmole) of 85% aqueous potassium hydroxide, 11 ml of water, 55 ml of ethanol and 5.5 ml of dioxane under argon at room temperature for 1 hour. Evaporate to a syrup and dilute with 25 ml of water. Charcoal and filter twice. Acidify with acetic acid. Separate the precipitate by filtration, wash with water and dry to obtain the title product (m.p. 302° C. dec.).

EXAMPLE 19

Methyl 11-Morpholinodibenzo[b,f][1,4]thiazepin-3-carboxylate 5,5-Dioxide

Reflux a mixture of 5.025 mg (15 mmole) of the 11-chloro ester of Example 14. 3.119 gm of morpholine and 75 ml of acetonitrile for 2 hours. Distill off the acetonitrile under a vacuum and dissolve the residue in 45 ml of methanol at room temperature. Filter, cool and separate the precipitate by filtration. Chromatograph over silica gel eluting with 1:4 ethylacetate in toluene. Recrystallize from ethanol to obtain the title product (m.p. 164°–166° C.).

EXAMPLE 20

11-Morpholinodibenzo[b,f][1,4]thiazepin-3-carboxylic Acid 5,5-Dioxide

Stir 386 mg (1 mmole) of the ester of Example 19 in a solution of 131.8 mg (2 mmole) of 85% aqueous potassium hydroxide, 1.3 ml of water, 6.5 ml of ethanol and 0.65 ml of dioxane at room temperature under argon for 1 hour. Evaporate to dryness and dissolve the residue in 5 ml of water. Acidify with acetic acid, separate the precipitate by filtration, wash with water and dry. Recrystallize from methanol to obtain the title product (m.p. 200–295 dec).

EXAMPLE 21

11-Piperidinodibenzo[b,f][1,4]thiazepin-3-carboxylic Acid 5,5-Dioxide

Repeat the process of Examples 19 and 20 substituting an equivalent quantity of piperidine for the morpholine employed in Example 19, in order to obtain the title product.

EXAMPLE 22

10,11-Dihydro-11-oxodibenzo[b,f][1,4]thiazepin-7-carboxylic Acid

Step A: 3-Mercapto-4-aminobenzoic Acid

Reflux 59 gm of 2-aminobenzothiazole-6-carboxylic acid (prepared by the procedure of Ann., 558, pg. 29, 1947) in a mixture of 300 gm of potassium hydroxide and 300 gm of water for 3½ hours. Cool and use in the next step as the dipotassium salt.

Step B: 4-Amino-3-(o-carboxyphenylthio)benzoic Acid

Reflux a mixture of 200 ml of the 50% potassium hydroxide solution of Step A, 24.15 gm (97 mmoles) of o-iodobenzoic acid and 7.5 gm of copper metal powder for 1½ hours. Cool the mixture and filter. Dilute the filtrate to twice its volume with water and acidify. Separate the solids by filtration, wash well with water and air dry.

Step C: 10,11-Dihydro-11-oxodibenzo[b,f][1,4]thiazepin-7-carboxylic Acid

Place 25.48 gm of the benzoic acid of Step B powered in a 500 ml flask under a nitrogen atmosphere. Heat to 250°–255° C. for 1½ hours. Scrape the solids from the flask and recrystallize from acetic acid to obtain the title product (m.p. changes crystalline forms at 325° C.- no melt to 360° C.).

EXAMPLE 23

Methyl 10,11-Dihydro-11-oxodibenzo[b,f][1,4]thiazepin-7-carboxylate

Dissolve 1 gm of the acid of Example 22 with heating in 100 ml of tetrahydrofuran. Filter and cool the filtrate to room temperature. Add 500 mg. of diazomethane and stir at room temperature for 30 minutes. Strip to dryness and triturate the residue in methanol. Recover the title product by filtration. (m.p. 240°–257° C.).

EXAMPLE 24

Methyl 10,11-Dihydro-11-oxodibenzo[b,f][1,4]thiazepin-7-carboxylate 5-Oxide

Suspend 1.14 gm (4 mmole) of the ester of Example 23 in 60 ml of methylene chloride and add 1.035 gm of commercial m-chloroperbenzoic acid. Stir at room temperature for 45 minutes and filter. Concentrate the filtrate and separate the solids. Combine the solids to obtain the title product (yield 1.21 gm).

EXAMPLE 25

10,11-Dihydro-11-oxodibenzo[b,f][1,4]thiazepin-7-carboxylic Acid 5-Oxide

Stir at room temperature 1.11 gm of the ester of Example 24 in a mixture of 50 ml of tetrahydrofuran and 50 ml of 10% aqueous sodium hydroxide for 3 hours. Separate the phases and extract the organic phase with 10% aqueous sodium hydroxide. Wash the combined aqueous phases with tetrahydrofuran and evaporate partially to remove residual tetrahydrofuran. Acidify with acetic acid. Separate the precipitate, wash with water and dry to obtain the title product (mp 352° C. dec).

EXAMPLE 26

Methyl 10,11-Dihydro-11-oxodibenzo[b,f][1,4]thiazepin-7-carboxylate 5,5-Dioxide

Dissolve 1.76 gm (6.175 mmole) of the ester of Example 23 in 250 ml of chloroform and add 3.76 gm of commercial m-chloroperbenzoic acid. Stir the mixture at room temperature for 44 hours. Filter and strip the filtrate to dryness. Dissolve the residue in methylene chloride and stir with excess calcium hydroxide for 5 minutes. Strip to dryness and dissolve the residue in methanol. Allow to stand for 48 hours and filter to obtain the title product (yield 745 mg.).

EXAMPLE 27

10,11-Dihydro-11-oxodibenzo[b,f][1,4]thiazepin-7-carboxylic Acid 5,5-Dioxide

Stir at room temperature 795 mg of the ester of Example 26 in a mixture of 50 ml of 10% aqueous sodium hydroxide and 50 ml of tetrahydrofuran for 3 hours. Separate the layers and extract the organic layer with 10% aqueous sodium hydroxide. Wash the combined aqueous layers with ether and acidify with acetic acid. Separate the precipitate by filtration, wash with water and dry in order to obtain the title product (m.p. 337°–340° C. with subsequent dec.).

EXAMPLE 28

Methyl 11-chlorodibenzo[b,f][1,4]thiazepin-7-carboxylate

Repeat the process of Example 6, substituting an equivalent quantity of the methyl 10,11-dihydro-11-oxodibenzo[b,f][1,4]thiazepin-3-carboxylate employed in Example 6, in order to obtain the title product.

EXAMPLE 29

10,11-dihydrodibenzo[b,f][1,4]thiazepin-7-carboxylic Acid

Repeat the processes of Examples 7 and 8, substituting an equivalent quantity of methyl 11-chlorodibenzo[b,f][1,4]thiazepin-3-carboxylate employed in Example 7, in order to obtain the title product.

EXAMPLE 30

Dibenzo[b,f][1,4]thiazepin-7-carboxylic Acid

Repeat the procedures of Examples 9 and 10, substituting an equivalent quantity of methyl 11-chlorodibenzo[b,f][1,4]thiazepin-7-carboxylate for the methyl 11-chlorodibenzo[b,f][1,4]thiazepin-3-carboxylate employed in Example 9, in order to obtain the title product.

EXAMPLE 31

Methyl 10,11-Dihydro-11-oxodibenzo[b,f][1,4]thiazepin-3-carboxylate

Step A: 3-Chlorocarbonyl-10,11-dihydro-11-oxodibenzo[b,f][1,4]thiazepine

Dissolve 5.16 gm of 10,11-dihydro-11-oxodibenzo[b,f][1,4]thiazepin-3-carboxylic acid in 100 cc of chloroform and 50 cc of thionyl chloride and add to the mixture 1.0 cc of dimethylformamide. Allow the mixture to stand at room temperature for 72 hours. Evaporate the mixture to dryness to obtain the desired acid chloride.

Step B: Methyl 10,11-dihydro-11-oxodibenzo[b,f][1,4]thiazepin-3-carboxylate

Dissolve 2.0 of the acid chloride of Step A in 20 cc of tetrahydrofuran containing 1.0 cc of methanol and 4 cc of pyridine. Allow the mixture to stand at room temperature for 24 hours then evaporate to dryness. Dissolve the residue in 1:4 ether/hexane and filter through silica gel. Evaporate the filtrate to dryness to obtain the title product.

Employing the process of Example 31, but substituting another lower alkanol such as, for example, ethanol, 2-propanol butanol and 2-butanol, for the methanol for Step B, the corresponding loweralkyl esters of 10,11-dihydro-11-oxodibenzo[b,f][1,4]thiazepin-3-carboxylic acid are obtained.

EXAMPLE 32

Methyl 10,11-dihydro-11-oxodibenzo[b,f][1,4]thiazepin-7-carboxylate

Repeat the process of Example 31, substituting 10,11-dihydro-11-oxodibenzo[b,f][1,4]thiazepin-7-carboxylic acid for the 10,11-dihydro-11-oxodibenzo[b,f][1,4]-thiazepin-3-carboxylic acid of Step A, in order to obtain the title product.

By substituting, where desired, other lower alkanols such as, for example, ethanol, 2-propanol, butanol and 2-butanol, for the methanol of Step B, the corresponding lower alkyl esters of 10,11-dihydro-11-oxodibenzo[b,f][1,4]thiazepin-7-carboxylic acid are obtained.

Loweralkyl esters of 10,11-dihydrobenzo[b,f][1,4]-thiazepin-3-(or 7)-carboxylic acid and dibenzo[b,f][1,4]-thiazepin-3(or 7)-carboxylic acid are prepared by following the process of Example 31 by substituting the desired 3-(or 7)-carboxylic acid for the starting material of Step A.

EXAMPLE 33

10,11-Dihydro-11-oxodibenzo[b,f][1,4]thiazepin-3-carboxamide

Step A: 3-Chlorocarbonyl-10,11-dihydro-11-oxodibenzo[b,f][1,4]thiazepin

Heat a solution of 5 gm. of 10,11-dihydro-11-oxodibenzo[b,f][1,4]thiazepin-3-carboxylic acid and 40 ml of thionyl chloride under reflux for 20 minutes. Evaporate the reaction mixture under vacuum to dryness. Repeat the evaporation with two 30 ml portions of carbon tetrachloride. Crystallize the residue from diisopropyl ether to obtain the title product.

Step B: 10,11-Dihydro-11-oxodibenzo[b,f][1,4]thiazepin-3-carboxamide

Dissolve the acid chloride from Step A in 20 ml. of dry tetrahydrofuran and add this solution dropwise with stirring to a cooled (ice-bath) saturated solution of ammonia in 60 ml of tetrahydrofuran. Pass ammonia through the reaction mixture simultaneously for 15 minutes. Stir at room temperature for an additional 15 minutes and evaporate the reaction mixture to dryness. Add a mixture of 12 ml of ethanol and 60 ml of water to the residue and stir at room temperature for an additional 30 minutes. Separate the solid by filtration and wash with water, then with ethanol and then with ether. Dry in vacuo to obtain the title product.

In a similar manner, substituting 10,11-dihydro-11-oxodibenzo[b,f][1,4]thiazepin-7-carboxylic acid for the 10,11-dihydro-11-oxodibenzo[b,f][1,4]thiazepin-3-carboxylic acid in Step A, there is obtained 10,11-dihydro-11-oxodibenzo[b,f][1,4]thiazepin-7-carboxamide. Carboxamides of 10,11-dihydrodibenzo[b,f][1,4]thiazepin-3(or 7)-carboxylic acid or dibenzo[b,f][1,4]thiazepin-3(or 7)-carboxylic acid are prepared by the process of Example 33, by substituting the desired 3(or 7) carboxylic acid for the starting material of Step A.

EXAMPLE 34

10,11-Dihydro-11-oxodibenzo[b,f][1,4]thiazepin-3N-methylcarboxamide

Add 6.0 gm of 3-chlorocarbonyl-10,11-dihydro-11-oxodibenzo[b,f][1,4]thiazepin to 4 gm. of methylamine in 100 ml of methylene chloride at 0°-5° C. Add 13 ml. of triethylamine dropwise over 10 minutes then stir the reaction mixture at room temperature overnight. Extract the reaction mixture with water, dry the organic layer and evaporate to dryness. Chromatograph over silica gel eluting with 200:20 toluene/dioxane. Evaporate eluate to dryness and recrystallize residue from methanol to obtain the title compound.

In a similar manner, substituting another N-loweralkylamine such as, for example, ethylamine, propylamine, isopropylamine, butylamine and the like, or a N,N-diloweralkylamine such as, for example, dimethylamine, diethylamine, dipropylamine, dibutylamine and the like, for the methylamine employed above, there is obtained the corresponding 10,11-dihydro-11-oxodibenzo[b,f][1,4]thiazepin-3-N-lower alkylcarboxamide or 2-N,N-diloweralkylcarboxamide. Corresponding 10,11-dihydro-11-oxodibenzo[b,f][1,4]thiazepin-7-carboxamides, 7-N-loweralkylcarboxamides and 7-N,N-diloweralkylcarboxamides are prepared by substituting 7-chlorocarbonyl-10,11-dihydro-11-oxodibenzo[b,f][1,4]thiazepin for the 3-chlorocarbonyl-10,11-dihydro-11-oxodibenzo[b,f][1,4]thiazepin employed above.

Also in a similar manner, substituting a carboxyloweralkylamine such as, for example, glycine, valing, leucine, isoleucine and the like or the N-loweralkyl derivatives thereof, such as for example, N-methylglycinyl, N-propylleucine, N-butylisoleucine and the like, there is obtained the corresponding 10,11-dihydro-11-oxodibenzo[b,f][1,4]thiazepin-3-(or 7)carboxyloweralkyl carboxamides or the N-loweralkyl derivatives thereof.

3-(or 7)-N-loweralkylcarboxamides, and carboxyloweralkylcarboxamides and the N-loweralkyl derivatives thereof corresponding to 10,11-dihydrodibenzo[b,f][1,4]thiazepin-3(or 7)-carboxylic acid and dibenzo[b,f][1,4]thiazepin-3(or 7)-carboxylic acid are prepared by following the process of Example 34 by substituting the desired 3-(or 7)-chlorocarbonyl compound for the starting material employed in Example 34.

EXAMPLE 35

10,11-Dihydro-11-oxodibenzo[b,f][1,4]thiazepin3-N-methanesulfonylcarboxamide

Heat 5.0 gm. of 10,11-dihydro-11-oxodibenzo[b,f][1,4]thiazepin-3-carboxylic acid in 50 cc of thionyl chloride for 15 minutes at reflux and then distill off the excess thionyl chloride. Evaporate the residue twice with small volumes of benzene. Add the resulting acid chloride to 4.0 gm. of methanesulphonamide in 100 ml. of methylene chloride at 0°-5° C. Add dropwise over 10 minutes 15 ml. of triethylamine. Stir the mixture at room temperature overnight. Extract the reaction mixture with 100 cc of 0.5 N sodium hydroxide, wash the alkaline extract with ether and acidify with 6 N hydrochloride acid. Separate the solids by filtration and dry in vacuo over potassium hydroxide. Chromatograph over silica gel eluting with 200:20:3 toluene/dioxane/acetic acid. Evaporate the eluate to dryness and recrystallize the residue from methanol to obtain the title product.

In a similar manner, substituting another loweralkylsulphonamide such as, for example, ethanesulphonamide, propanesulphonamide, butanesulphonamide and the like, for the methanesulphonamide employed above, there is obtained the corresponding 10,11-dihydro-11-oxodibenzo[b,f][1,4]thiazepin-2-N-loweralkylsulfonylcarboxamide. Corresponding 10,11-dihydro-11-oxodibenzo[b,f][1,4]thiazepin-7-N-loweralkylsulfonylcarboxamides are prepared by substituting 10,11-dihydro-11-oxodibenzo[b,f][1,4]thiazepin-7-carboxylic acid for the 10,11-dihydro-11-oxodibenzo[b,f][1,4]thiazepin-3-carboxylic acid employed above.

3-(or 7)-N-loweralkylsulfonylcarboxamide derivatives of 10,11-dihydrodibenzo[b,f][1,4]thiazepin-3(or 7)-carboxylic acid and dibenzo[b,f][1,4]thiazepin-3(or 7)-carboxylic acid are prepared by following the procedure of Example 35 by substituting the desired 3-(or 7)-carboxylic acid for the carboxylic acid starting material in Example 35.

EXAMPLE 36

10,11-Dihydro-11-oxodibenzo[b,f][1,4]thiazepin-3-(3-methyl-2-thiazolidinylidine)carboxamide Reflux 1.0 gm. of 10,11-dihydro-11-oxodibenzo[b,f][1,4]thiazepin-3-carboxylic acid in 15 cc of thionyl chloride for 30 minutes. Strip the reaction mixture to dryness and dissolve the residue in 25 cc of methylene chloride. Add a solution of 1.0 gm. of 2-imino-3-methylthiazolidine in 10 cc of methylene chloride. Stir at room temperature for 30 minutes and add water. Continue stirring for 10 minutes. Separate the organic phase and wash with water and dry overnight over sodium sulfate. Strip to dryness. Stir and triturate the residue in ether, then in methanol. Chromatograph the resulting solid over silica gel, eluting with 20% ethyl acetate in benzene. Strip to dryness to obtain the title product.

3-(or 7)-(3-methyl-2-thiazolidinylidine)carboxamides corresponding to 10,11-dihydrodibenzo[b,f][1,4]thiazepin-3(or 7)-carboxylic acid and dibenzo[b,f]thiepin-3-carboxylic acid are prepared by following the procedure of Example 36 by substituting the desired 3-(or 7)-carboxylic acid for the starting material employed in Example 36.

EXAMPLE 37

3-(4-Hydroxy-Δ³-pyrrolin-3-yl-2,5-dione)-10,11-Dihydro-11-oxodibenzo[b,f][1,4]thiazepine Step A:
3-Hydroxymethyl-10,11-dihydro-11-oxodibenzo[b,f][1,4]thiazepine Dissolve 5.1 gm. of 10,11-dihydro-11-oxodibenzo[b,f][1,4]thiazepin-3-carboxylic acid in 100 cc. of tetrahydrofuran and add 35 cc. of 1 M borane in tetrahydrofuran at room temperature under a nitrogen atmosphere. Stir the mixture at room temperature for 3 hours. Slowly dilute the reaction mixture with water and then with ethyl acetate. Wash with aqueous sodium chloride, dry and evaporate to an oil.

Step B:
3-Bromomethyl-10,11-dihydro-11-oxodibenzo[b,f][1,4]thiazepine

Dissolve 4.43 gm. of the alcohol of Step A in 100 cc. of benzene and add 1 cc (10.5 mmole) of phosphorous tribromide. Stir at room temperature for 1 hour, add water and then dilute with toluene. Wash three times with water, dry and strip to a solid residue.

Step C:
3-Cyanomethyl-10,11-dihydro-11-oxodibenzo[b,f][1,4]thiazepine

Dissolve 6.4 gm. of the bromide of Step B in 75 cc. of dimethylformamide and add 2.95 gm. of sodium cyanide. Stir the mixture at room temperature for 1.5 hours. Dilute with 600 cc. of water and extract three times with ether. Wash the combined organics with water, dry and strip to a solid residue. Triturate in hexane and recover the solid by filtration.

Step D:
10,11-Dihydro-11-oxodibenzo[b,f][1,4]thiazepin-3-acetic Acid

Reflux 2.0 gm. of the nitrile of Step C in a mixture of 30 cc. of 20% aqueous sodium hydroxide and 30 cc. of ethanol for four hours. Strip away the alcohol, wash with ethyl acetate and acidify the aqueous phase with hydrochloric acid. Separate the precipitate by filtration. Wash with water and dry.

Step E:
10,11-Dihydro-11-oxodibenzo[b,f][1,4]thiazepin-3-acetamide

Reflux for 20 minutes a mixture of 5.0 gm. of the acid of Step D and 40 ml of thionyl chloride. Evaporate to dryness under vacuum. Evaporate twice with 30 ml portions of carbon tetrachloride. Dissolve the residue in 20 ml. of tetrahydrofuran and add the solution dropwise to a cooled and stirred saturated solution (ice bath) of ammonia in 60 ml. of tetrahydrofuran. Pass ammonia through the solution simultaneously. Continue stirring at room temperature for an additional 15 minutes. Evaporate the mixture to dryness. Add a mixture of 12 ml. of ethanol and 60 ml. of water and stir the suspension for 30 minutes. Separate the solids and wash with water, then with ethanol and finally with ether to obtain the title product.

Step F:
3-(4-Hydroxy-Δ$^3$-pyrrolin-3-yl-2,5-dione)-10,11-Dihydro-11-oxodibenzo[b,f][1,4]thiazepine Stir at room temperature a mixture of 5.118 gm. of the amide of Step E, 2.939 gm. of diethyl oxalate, 4.723 gm. of potassium t-butoxide and 40 ml. of dimethylformamide for 6 hours. Pour the reaction mixture into 300 ml. of ice-water and extract with 300 ml. of ethyl acetate. Acidify with 6 N hydrochloric acid and separate the ethylacetate layer. Wash with saturated sodium chloride solution and dry. Evaporate to dryness and dissolve the residue in warm dioxane. Treat with a slight excess of ammonia and separate the solid by filtration. Wash with dioxane and dry. Suspend the product in water, acidify with 6 N hydrochloric acid and extract with ethyl acetate. Wash the extract with saturated sodium chloride solution, dry over magnesium sulfate and evaporate to obtain the title product.

In a similar manner, substituting 10,11-dihydrodibenzo[b,f][1,4]thiazepin-3-(or 7)-carboxylic acid or dibenzo[b,f][1,4]thiazepin-3-(or 7)-carboxylic acid for the carboxylic acid starting material employed in Step A, there is obtained the corresponding 3-(or 7)-(4-hydroxy-Δ$^3$-pyrrolin-3-yl-2,5-dione)-10,11-dihydrodibenzo[b,f][1,4]thiazepine or 3-(or 7)-(4-hydroxy-Δ$^3$-pyrrolin-3-yl-2,5-dione)-dibenzo[b,f][1,4]thiazepine.

EXAMPLE 38

β-Hydroxyethyl 10,11-Dihydro-11-oxodibenzo[b,f][1,4]thiazepin-3-carboxylate

To a stirred solution of 1.0 gm. of 2-chlorocarbonyl-10,11-dihydro-11-oxodibenzo[b,f][1,4]thiazepin in 50 cc. of methylene chloride, add 3 gm. of ethylene glycol and stir the mixture for 18 hours at room temperature. Distill off the solvent and excess ethylene glycol under high vacuum (0.1 mm.). Chromatograph the residue on a silica gel column (100 gm.), eluting with 10% ethyl acetate in benzene to obtain the title product.

In a similar manner, substituting another loweralkyldiol such as, for example, trimethylene glycol and 1,4-butanediol and the like for the ethylene glycol, there is obtained the corresponding hydroxyloweralkylester. The corresponding hydroxyloweralkyl 7-carboxylate esters are prepared by substituting 7-chlorocarbonyl 10,11-dihydro-11-oxodibenzo[b,f][1,4]thiazepine for the 2-chlorocarbonyl 10,11-dihydro-11-oxodibenzo[b,f][1,4]thiazepine employed above.

Hydroxyloweralkylesters of 10,11-dihydrodibenzo[b,f][1,4]thiazepin-3-(or 7)-carboxylic acid and dibenzo[b,f][1,4]thiazepin-3-(or 7)-carboxylic acid are prepared by substituting the desired 3-(or 7)-carboxylic acid for the starting material employed in Example 38.

EXAMPLE 39

β-Dimethylaminoethyl-10-11-dihydro-11-oxodibenzo[b,f][1,4]thiazepin-3-carboxylate Dissolve 1.0 gm. of 3-chlorocarbonyl-10-11-dihydro-11-oxodibenzo[b.f][1,4]thiazepin as prepared in Example 31, Step A, in 10 cc. of anhydrous tetrahydrofuran with stirring and add 2 ml. of N,N-dimethylethanolamine. Stir at room temperature for 18 hours and strip the mixture to dryness. Partition the residue between ether and dilute hydrochloric acid and separate the aqueous layer. Basify the aqueous layer with aqueous ammonia and extract with ethyl acetate. Evaporate the organic phase and chromatograph the residue over silica-gel eluting with 90% chloroform in methanol to obtain the title product.

In a similar manner, substituting another N,N-diloweralkylaminoloweralkanol such as, for example, diethylethanolamine, 3-N,N-dimethylaminopropan-1-ol, 4-N,N-diethylaminobutan-1-ol and the like, for the N,N-dimethylethanolamine, there is obtained the corresing N,N-diloweralkylaminoloweralkylester. The corresponding N,N-diloweralkyl-7-carboxylate esters are prepared by substituting 7-chlorocarbonyl 10,11-dihydro-11-oxodibenzo[b,f][1,4]thiazepine for the 3-chlorocarbonyl-10,11-dihydro-11-oxodibenzo[b,f][1,4]thiazepine employed above.

N,N-diloweralkylaminoloweralkyl esters of 10,11-dihydrodibenzo[b,f][1,4]thiazepin-3-(or 7)-carboxylic acid and dibenzo[b,f][1,4]thiazepin-3-(or 7)-carboxylic acid are prepared by following the procedure of Example 39 and substituting the desired 3-(or 7)-chlorocarbonyl compound for the chlorocarbonyl starting material employed in Example 39.

EXAMPLE 40

10,11-Dihydro-11-oxodibenzo[b,f][1,4]thiazepin-3-N-carboxymethylcarboxamide

Reflux 1.0 gm. of 3-chlorocarbonyl-10,11-dihydro-11-oxodibenzo[b,f][1,4]thiazepin in 20 cc. of ethyl acetate containing 2.0 gm. of glycine for 5 hours. Evaporate the mixture to dryness. Add 30 cc. of water to the solid residue and stir at room temperature for one hour. Separate the solid by filtration and recrystallize from ethanol to obtain the title product.

In a similar manner, substituting another amino acid such as, for example, alanine or valine and the like for the glycine, there is obtained the corresponding 3-carboxyloweralkylcarboxamide.

The corresponding 7-carboxyloweralkylcarboxamides are prepared by substituting 7-chlorocarbonyl 10,11-dihydro-11-oxodibenzo[b,f][1,4]thiazepine for the 3-chlorocarbonyl 10,11-dihydro-11-oxodibenzo[b,f][1,4]thiazepine employed above.

Carboxyloweralkylcarboxamides of 10,11-dihydrodibenzo[b,f][1,4]thiazepin-3(or 7)-carboxylic acid and dibenzo[b,f][1,4]thiazepin-3(or 7)-carboxylic acid are prepared by substituting the desired 3-(or 7)-chlorocarbonyl compound for the starting material employed in Example 40.

EXAMPLE 41

β-Carboxyethyl 10,11-Dihydro-11-oxodibenzo[b,f][1,4]thiazepin-3-carboxylate

Dissolve 1.0 gm. of 3-chlorocarbonyl-10,11-dihydro-11-oxodibenzo[b,f][1,4]thiazepine in 20 cc. of tetrahydrofuran and add 1.0 gm. of the sodium salt of β-hydroxypropionic acid. Stir the mixture at room temperature for 18 hours. Filter and evaporate the filtrate to dryness. Recrystallize the solid residue from ethanol to obtain the title product.

In a similar manner, substituting another hydroxyloweralkanoic acid salt such as, for example, an alkali metal salt or hydroxyacetic acid, 3-hydroxybutyric acid and the like, for the β-hydroxypropionic acid sodium salt, there is obtained the corresponding carboxyloweralkyl-3-carboxylate ester. The corresponding carboxyloweralkyl-7-carboxylate esters are prepared by substituting 7-chlorocarbonyl-10,11-dihydro-11-oxodibenzo[b,f][1,4]thiazepin for the 3-chlorocarbonyl-10,11-dihydro-11-oxodibenzo[b,f][1,4]thiazepin employed above.

Carboxyloweralkyl-3-(or 7)-carboxylate esters of 10,11-dihydrodibenzo[b,f][1,4]thiazepin3(or 7)-carboxylic acid and dibenzo[b,f][1,4]thiazepin-3(or 7)-carboxylic acid are prepared by substituting the desired 3-(or 7)-chlorocarbonyl compound for the starting material employed in Example 41.

EXAMPLE 42

3-(3-Hydroxy-1,2,5-thiadiazol-4-yl)-10,11-dihydro-11-oxo-dibenzo[b,f][1,4]thiazepin Step A:
3-Cyano-10,11-dihydro-11-oxodibenzo[b,f][1,4]thiazepin Stir 5 gm. of methyl 10,11-dihydro-11-oxodibenzo[b,f][1,4]thiazepin-3-carboxylate in 500 ml. of methanol saturated with ammonia gas for 24 hours at room temperature. Evaporate the reaction mixture to dryness. Reflux the residue in 200 ml. of methylene chloride containing 10 gm. of phosphorous oxychloride for eight hours. Cool the reaction mixture to room temperature and shake several times with water. Separate the organic layer, dry over magnesium sulfate and evaporate to dryness to obtain the title product.

Step B:
10,11-Dihydro-11-oxodibenzo[b,f][1,4]thiazepin-3-carboxaldehyde

Heat a mixture of 5.0 gm. of 3-cyano-10,11-dihydro-11-oxodibenzo[b,f][1,4]thiazepin and 4.0 gm. of Raney nickel alloy in 60 ml. of 75% (v/v) aqueous formic acid at reflux for 1.5 hours. Cool to room temperature and filter. Concentrate to small volume and extract with methylene chloride. Wash the extract with water and with 1 N sodium bicarbonate until neutral. Dry the neutral extract over sodium sulfate and concentrate to dryness to obtain the title product.

Step C:
10,11-Dihydro-11-oxodibenzo[b,f][1,4]thiazepin-3-(2-aminoacetonitrile)

Stir at room temperature for 12 hours a mixture of 5.85 gm. of ammonium chloride, 5.3 gm. of sodium cyanide, 75 ml. of ammonium hydroxide, 100 ml. of ethanol saturated with ammonia and 12 gm. of carboxaldehyde of Step A. Pour the reaction mixture into 300 ml. of water and extract with ether. Dry the extract over sodium sulfate and concentrate to dryness to obtain the title product.

Step D:
10,11-Dihydro-11-oxodibenzo[b,f][1,4]thiazepin-3-(2-aminoacetamide)

Stir at room temperature 5.0 gm. of the aminoacetonitrile of Step B in 30 ml. of concentrated hydrochloric acid for 300 minutes. Slowly pour the reaction mixture into cold ammonium hydroxide. Extract the mixture with ether and dry over sodium sulfate. Evaporate the extract to dryness to obtain the title product.

Step E:
3-(3-Hydroxy-1,2,5-thiadiazol-4-yl)-10,11-dihydro-11-oxodibenzo[b,f][1,4]thiazepine Stir overnight at room temperature a mixture of 1.365 gm. of the aminoacetamide of Step C, 1,989 gm. of sulfur monochloride and 5 ml. of dimethylformamide. Filter the reaction mixture and then partition between ice-water (75 ml.) and ethyl acetate (75 ml.). Filter, separate the organic layer, wash with saturated aqueous sodium chloride solution and dry over magnesium sulfate. Evaporate to dryness and dissolve the residue in 200 ml. of boiling ethanol, treat with charcoal and filter. Concentrate to 25 ml. and separate the solids by filtration to obtain the title product.

By substituting 7-cyano-10,11-dihydrodibenzo[b,f][1,4]thiazepin for the 3-cyano-10,11-dihydro-11-oxodibenzo[b,f][1,4]thiazepin employed in Step B above, there is obtained the corresponding 7-(3-hydroxy-1,2,5-thiaziazol)-4-yl-10,11-dihydro-11-oxodibenzo[b,f][1,4]thiazepine. Similarly, by substituting 3(or 7)-cyano-10,11-dihydrodibenzo[b,f][1,4]thiazepin or 3(or 7)-cyanodibenzo[b,f][1,4]thiazepin for the 3-cyano-10,11-dihydro-11-oxo-dibenzo[b,f][1,4]thiazepine employed in Step B, there is obtained the corresponding 3(or 7)-(3-hydroxy-1,2,5-thiaziazol-4-yl)-10,11-dihydro-11-oxodibenzo[b,f][1,4]thiazepine or 3-(or 7)-(3-hydroxy-1,2,5thiaziazol-4-yl-dihydrodibenzo[b,f][1,4]thiazepine. The required cyano intermediates are prepared by substituting the appropriate 3-(or 7)-carboxylic acid methyl ester for the methyl 10,11-dihydro-11-oxodibenzo[b,f][1,4]thiazepin-3-carboxylate employed in Step A above.

EXAMPLE 43

3-(1H-Tetrazol-5-yl)-10,11-dihydro-11-oxodibenzo[b,f][1,4]thiazepine

Heat a mixture of 800 mg. of 3-cyano-10,11-dihydro-11-oxodibenzo[b,f][1,4]thiazepine, 293 mg. of sodium azide and 265 mg. of ammonium chloride in 25 ml. of dimethylformamide at 130°–135° C. for 6 hours. Dilute the mixture with water and excess sodium carbonate. Extract with ethyl acetate. Acidify the aqueous phase and separate the precipitate by filtration to obtain the title product.

By substituting 7-cyano-10,11-dihydro-11-oxodibenzo[b,f][1,4]thiazepine for the 3-cyano starting material employed above, there is obtained the corresponding 7-(1H-tetrazol-5-yl)-10,11-dihydro-11-oxodibenzo[b,f][1,4]thiazepine. Similarly by substituting 3(or 7)-cyano-10,11-dihydrodibenzo[b,f][1,4]thiazepine or 3(or 7)-cyanodibenzo[b,f][1,4]-thiazepine for the 3-cyano starting material employed above, there is obtained the corresponding 3-(or 7)-(1H-tetrazol-5-yl)-10,11-dihydrodibenzo[b,f][1,4]thiazepine or 3(or 7)-(1H-tetrazol-5-yl)-dibenzo[b,f][1,4]thiazepine.

EXAMPLE 44

3(1H-Tetrazol-5-ylmethyl)-10,11-dihydro-11-oxodibenzo[b,f][1,4]thiazepine

Add to 25 cc of tetrahydrofuran cooled in an ice bath 1.59 gm. (11.9 mmole) of aluminum chloride, 1.33 gm. (5.25 mmole) of 3-cynaomethyl-10,11-dihydro-11-oxodibenzo[b,f][1,4]-thiazepine and 1.55 gm. (23.8 mmole) of sodium azide. Reflux the mixture for 19 hours, cool, dilute with water and acidify. Extract the mixture into ethyl acetate and evaporate. Triturate the residue in ether and separate the title product by filtration.

EXAMPLE 45

10,11-Dihydro-11-oxodibenzo[b,f][1,4]thiazepin-3-acetic Acid-11,11-Dioxide

Heat 600 mg. of 10,11-dihydro-11-oxodibenzo[b,f][1,4]thiazepin-3-acetic acid to 80°–85° C. in a mixture of 30 cc. of glacial acetic acid and 5 cc. of 30% hydrogen peroxide for 3 hours. Dilute with water to a final volume of about 250 cc. Separate the title product by filtration.

Although the instant invention has been described in the foregoing specification in terms of the use of the novel thiazepines disclosed herein in the treatment and control of human and warm-blooded animal disease conditions characterized by excessive undesirable contractile activity of prostaglandins and prostaglandin biosynthetic intermediates, and particularly of asthma, it will be recognized by those skilled in the art that, in addition to the involvement of contractile prostaglandins in chromic obstructive lung disease (e.g. asthma), prostaglandins play a role in other allergic conditions as well as in inflammation, diarrhea, hypertension, angina, cerebral spasm, premature abortion and dismenorrhea. Also, the thiazepines of this invention are potent $TXA_2$ biosynthesis inhibitors, inhibiting platelate aggregation, and can be useful in diseases such as atherosclerosis, variant anginal and myocardial infarction. Applicants consider application of the thiazepines disclosed and claimed herein to the treatment and control of such disease conditions to be obvious equivalents to the invention as disclosed by applicants and to fall within the scope of the instant invention.

The subject matter which applicants regard as their invention, and which is sought to be patented herein, is particularly pointed out and distinctly claimed as follows.

What is claimed is:

1. A compound selected from the group consisting of dibenzo[b,f]thiezepines having the structural formulae:

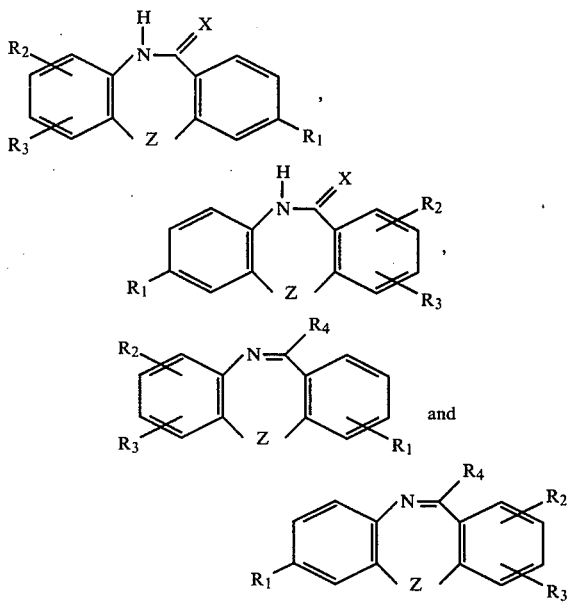

wherein
  Z is a member selected from the group consisting of thio, sulfinyl and sulfonyl;
  X is a member selected from the group consisting of O and $H_2$;
  $R_4$ is a member selected from the group consisting of hydrogen, and morpholino;
  $R_2$ and $R_3$ are the same or different and are members selected from the group consisting of hydrogen, halogen, nitro, loweralkyl, amino, N-loweralkylamino, N,N-diloweralkylamino, loweralkanoyl, hydroxy, loweralkoxy, loweralkylthio, trifluoromethylthio, loweralkylsulfinyl, loweralkylsulfonyl and trifluoromethyl; and
  $R_1$ is

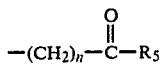

wherein n is an integer between 0 and 4;

$R_5$ is a member selected from the group consisting of hydroxy, loweralkoxy, N,N-diloweralkylaminoloweralkoxy, hydroxyloweralkoxy, carboxyloweralkoxy, amino, N-loweralkylamino, N,N-diloweralkylamino, loweralkylsulfonylamino, carboxyloweralkylamino and carboxamidoloweralkylamino, and the pharmaceutically acceptable salts thereof.

2. A compound of claim 1 wherein Z is thio and $R_5$ is hydroxy or loweralkoxy.

3. A compound of claim 1 wherein Z is thio and $R_1$ is

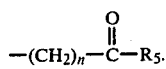

4. A compound of claim 1 wherein Z is thio; $R_2$, $R_3$, and $R_4$ are hydrogen; and $R_1$ is

5. A compound of claim 1 wherein Z is sulfinyl; $R_2$, $R_3$, and $R_4$ are hydrogen; and $R_1$ is

6. A compound of claim 1 wherein Z is sulfonyl; $R_2$, $R_3$, and $R_4$ are hydrogen; and $R_1$ is

7. A compound of claim 4 wherein $R_5$ is hydroxy.

8. The compound of claim 7 which is 10,11-dihydro-11-oxodibenzo[b,f][1,4]thiazepin-3-carboxylic acid.

9. The compound of claim 7 which is 10,11-dihydro-11-oxodibenzo[b,f][1,4]thiazepin-7-carboxylic acid.

10. The compound of claim 7 which is 10,11-dihydrodibenzo[b,f][1,4]thiazepin-3-carboxylic acid.

11. The compound of claim 7 which is 10,11-dihydrodibenzo[b,f][1,4]thiazepin-7-carboxylic acid.

12. The compound of claim 7 which is dibenzo[b,f][1,4]thiazepin-3-carboxylic acid.

13. The compound of claim 7 which is dibenzo[b,f][1,4]thiazepin-7-carboxylic acid.

14. The compound of claim 5 which is 10,11-dihydro-11-oxodibenzo[b,f][1,4]thiazepin-3-carboxylic acid 5-oxide.

15. The compound of claim 5 which is 10,11-dihydro-11-oxodibenzo[b,f][1,4]thiazepin-7-carboxylic acid 5-oxide.

16. The compound of claim 6 which is 10,11-dihydro-11-oxodibenzo[b,f][1,4]thiazepin-3-carboxylic acid 5,5-dioxide.

17. The compound of claim 6 which is 10,11-dihydro-11-oxodibenzo[b,f][1,4]thiazepin-7-carboxylic acid 5,5-dioxide.

18. The compound of claim 6 which is 10,11-dihydrodibenzo[b,f][1,4]thiazepin-3-carboxylic acid 5,5-dioxide.

19. The compound of claim 6 which is 10,11-dihydrodibenzo[b,f][1,4]thiazepin-7-carboxylic acid 5,5-dioxide.

20. The compound of claim 6 which is dibenzo[b,f][1,4]thiazepin-3-carboxylic 5,5-dioxide.

21. The compound of claim 6 which is dibenzo[b,f][1,4]thiazepin-7-carboxylic acid 5,5-dioxide.

* * * * *